United States Patent
Zelmanovic et al.

(10) Patent No.: US 6,524,858 B1
(45) Date of Patent: Feb. 25, 2003

(54) SINGLE CHANNEL, SINGLE DILUTION DETECTION METHOD FOR THE IDENTIFICATION AND QUANTIFICATION OF BLOOD CELLS AND PLATELETS IN A WHOLE BLOOD SAMPLE USING AN AUTOMATED HEMATOLOGY ANALYZER

(75) Inventors: David Zelmanovic, Monsey, NY (US); Valentine Jones, Malahide (IE)

(73) Assignee: Bayer Corporation, Tarrytown, NY (US)

(*) Notice: Subject to any disclaimer, the term of this patent is extended or adjusted under 35 U.S.C. 154(b) by 0 days.

(21) Appl. No.: 09/539,568

(22) Filed: Mar. 31, 2000

Related U.S. Application Data

(60) Provisional application No. 60/127,209, filed on Mar. 31, 1999.

(51) Int. Cl.[7] .......................... G01N 33/48; G01N 21/00
(52) U.S. Cl. ............................... 436/10; 436/8; 436/17; 436/18; 436/63; 436/66; 436/164; 436/166; 436/172; 436/174; 435/2; 422/73; 422/82.05; 422/82.08; 422/82.09
(58) Field of Search ............................... 436/8, 10, 17, 436/18, 63, 66, 164, 166, 172, 174; 435/2; 252/408.1; 422/73, 82.05, 82.08, 82.09

(56) References Cited

U.S. PATENT DOCUMENTS

| | | | |
|---|---|---|---|
| 4,727,020 A | | 2/1988 | Recktenwald .................. 435/6 |
| 4,735,504 A | * | 4/1988 | Tycko .......................... 356/336 |
| 4,882,284 A | | 11/1989 | Kirchanski et al. ............ 436/63 |
| 5,284,771 A | * | 2/1994 | Fan et al. ...................... 436/10 |
| 5,350,695 A | * | 9/1994 | Colella et al. ................. 436/10 |

(List continued on next page.)

FOREIGN PATENT DOCUMENTS

| | | |
|---|---|---|
| EP | 0 545 314 A1 | 6/1993 |
| EP | 0 678 743 A1 | 10/1995 |
| EP | 0 869 347 A2 | 10/1998 |

OTHER PUBLICATIONS

Shapiro et al., (1976), "Combined Blood Cell Counting and Classification with Fluorochrome Stains and Flow Instrumentation", *J. Histochemistry and Cytochemistry*, 24:396–411.

(List continued on next page.)

*Primary Examiner*—Maureen M. Wallenhorst
(74) *Attorney, Agent, or Firm*—Morgan & Finnegan, LLP

(57) ABSTRACT

The invention provides a new single channel, single dilution method and system for identifying, analyzing and quantifying the cellular components of whole blood using a single channel, rather than multiple channels, of an automated hematology analyzer utilizing flow cytometry and the detection of the light scattered and absorbed by each cell. The single channel utilized in the method was previously known and used only for red blood cell and reticulocyte analysis. The method involves the use of an organic dye in the reagent solution for staining the nucleic acid of reticulocytes, including reticulated platelets, and white blood cells in the sample. The single channel method developed and described is particularly useful for determining white blood cell counts and assessing parameters of a whole blood sample, for blood samples from both human and non-human mammals. The single channel method of the invention employs only one blood diluent reagent composition that is mixed with the blood sample aliquot for analysis and, optimally, a sheath/rinse reagent, thus making it simpler and easier to use. In addition, the reagent compositions of the method are more benign to the white blood cells than previous reagents, which contained various lytic surfactants for removing red blood cells, for example. The apparatus for performing the method provides an economical, streamlined and space-saving analyzer for carrying out complete blood cell analysis on a mammalian whole blood sample.

185 Claims, 11 Drawing Sheets

U.S. PATENT DOCUMENTS

| | | | | |
|---|---|---|---|---|
| 5,360,739 A | * | 11/1994 | Fan et al. | 435/29 |
| 5,411,891 A | * | 5/1995 | Fan et al. | 435/2 |
| 5,438,003 A | * | 8/1995 | Colella et al. | 435/2 |
| 5,627,037 A | | 5/1997 | Ward et al. | 435/7.21 |
| 5,817,519 A | * | 10/1998 | Zelmanovic et al. | 356/336 |
| 5,830,764 A | * | 11/1998 | Sorette | 435/2 |
| 5,888,752 A | * | 3/1999 | Malin et al. | 422/1 |
| 6,060,322 A | * | 5/2000 | Horton et al. | 435/2 |
| 6,114,173 A | * | 9/2000 | Zelmanovic et al. | 252/408.1 |
| 6,197,593 B1 | * | 3/2001 | Deka et al. | 356/39 |

OTHER PUBLICATIONS

V. Ost et al, (1998), "Flow Cytometric Differentiation of Erythrocytes and Leukocytes in Dilute Whole Blood by Light Scattering", *Cytometry,* 32:191–197.

* cited by examiner

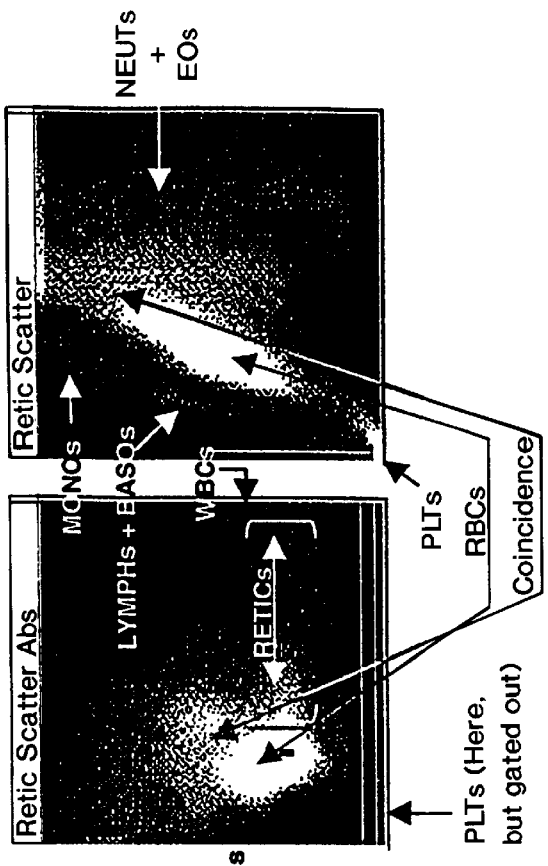

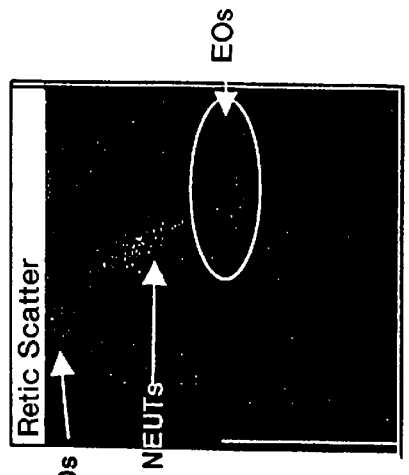
FIG. 2A  FIG. 2B  FIG. 2C
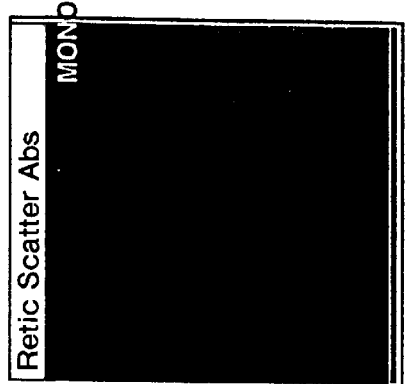
Sum of 10 aspirations
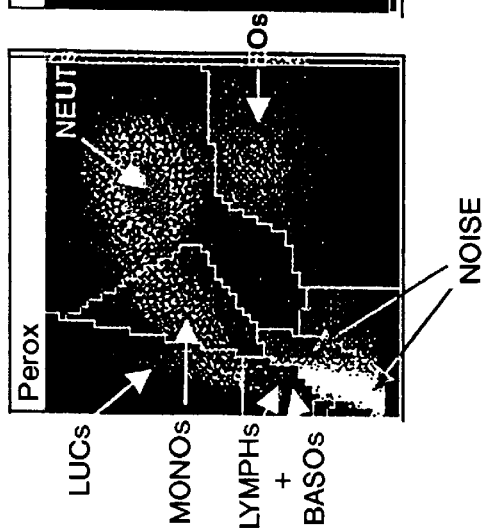
| WBC Differential | % | ×10³ cells/μL | |
|---|---|---|---|
| WBC: | | L 4.90 | × |
| Neut: | 57.0 | 2.80 | × |
| Lymph: | 28.2 | 1.38 | × |
| Mono: | 7.2 | 0.35 | × |
| Eos: | 3.2 | 0.16 | × |
| Baso: | 1.0 | 0.05 | |
| LUC: | 3.4 | 0.17 | × |
| LI: | | 2.25 | |
| MPXI: | | −4.3 | |

| WBC Differential | | |
|---|---|---|
| | % | ×10³ cells/μL |
| WBC: | | 5.40 |
| Neut: | 66.9 × | 3.61 × |
| Lymph: | 23.3 × | 1.26 × |
| Mono: | 4.7 × | 0.26 × |
| Eos: | 1.8 × | 0.10 × |
| Baso: | 0.3 | 0.01 |
| LUC: | 3.0 × | 0.16 × |
| LI: | | 2.13 |
| MPXI: | | 3.5 |

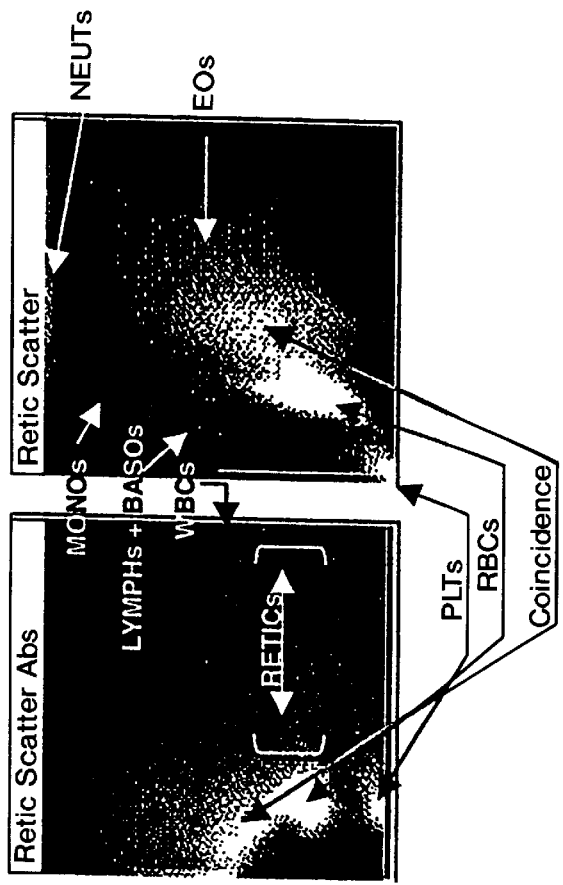

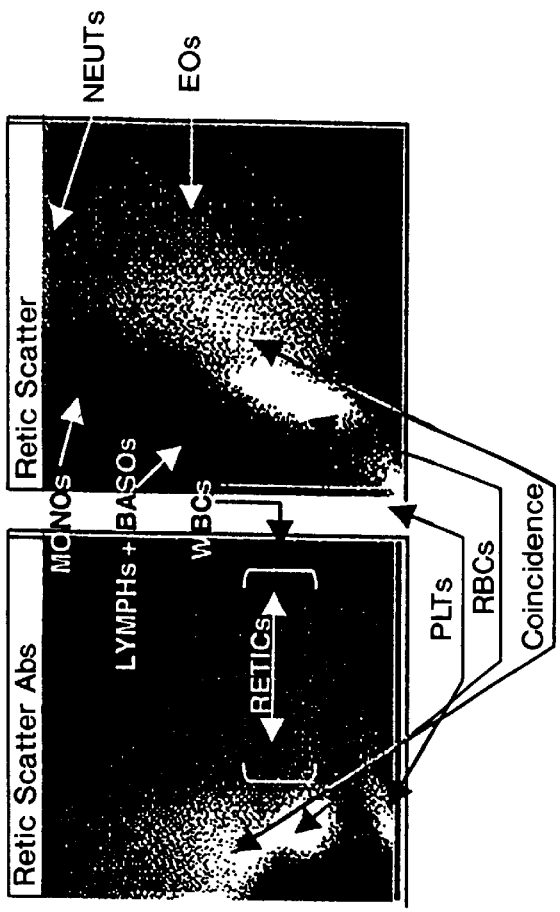
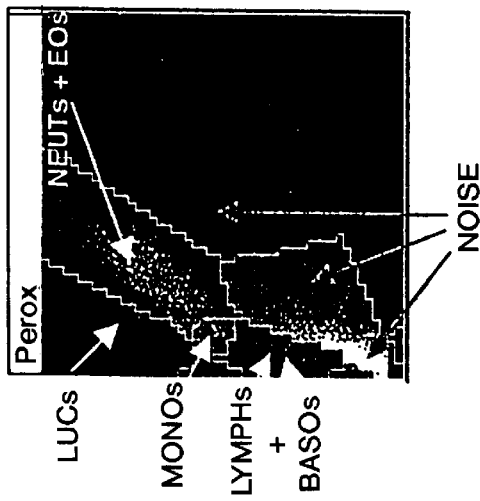
FIG. 5A  FIG. 5B  FIG. 5C

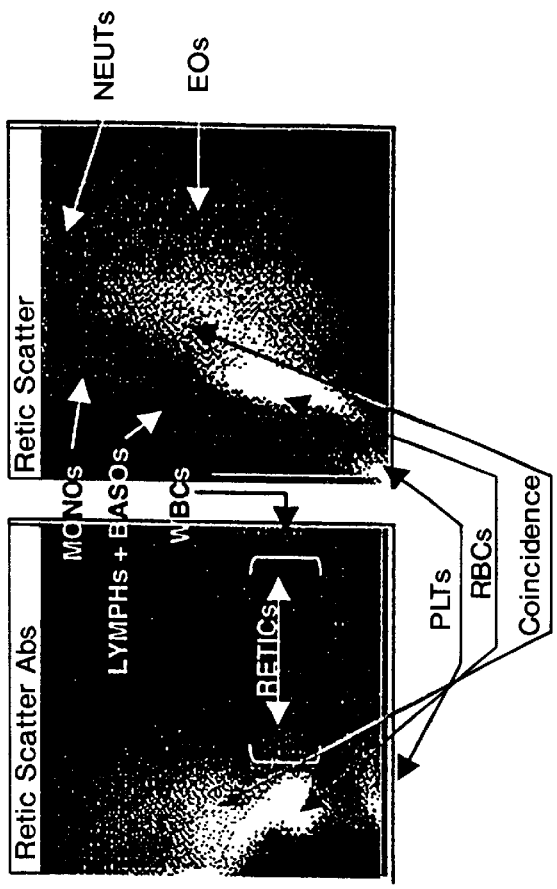

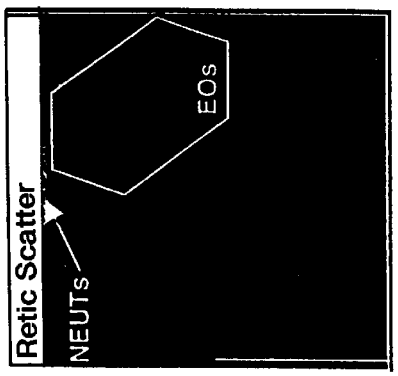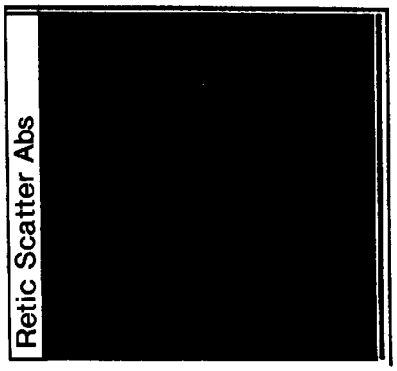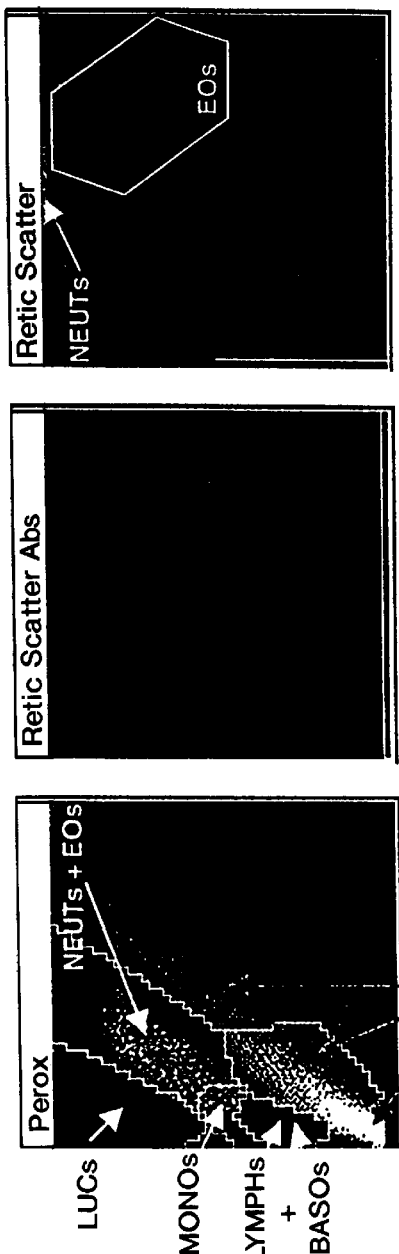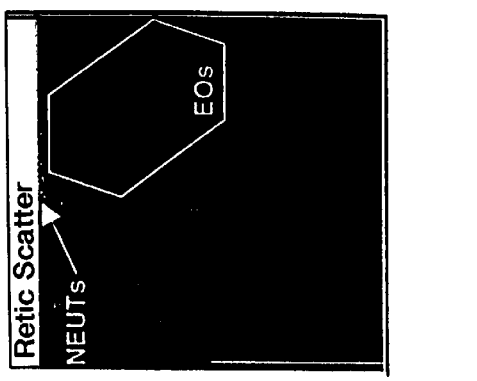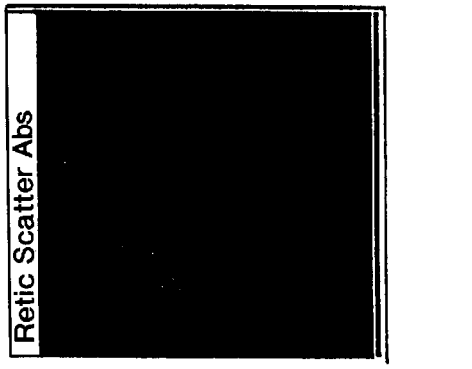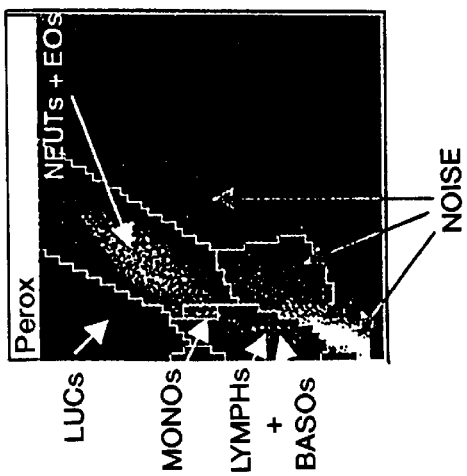

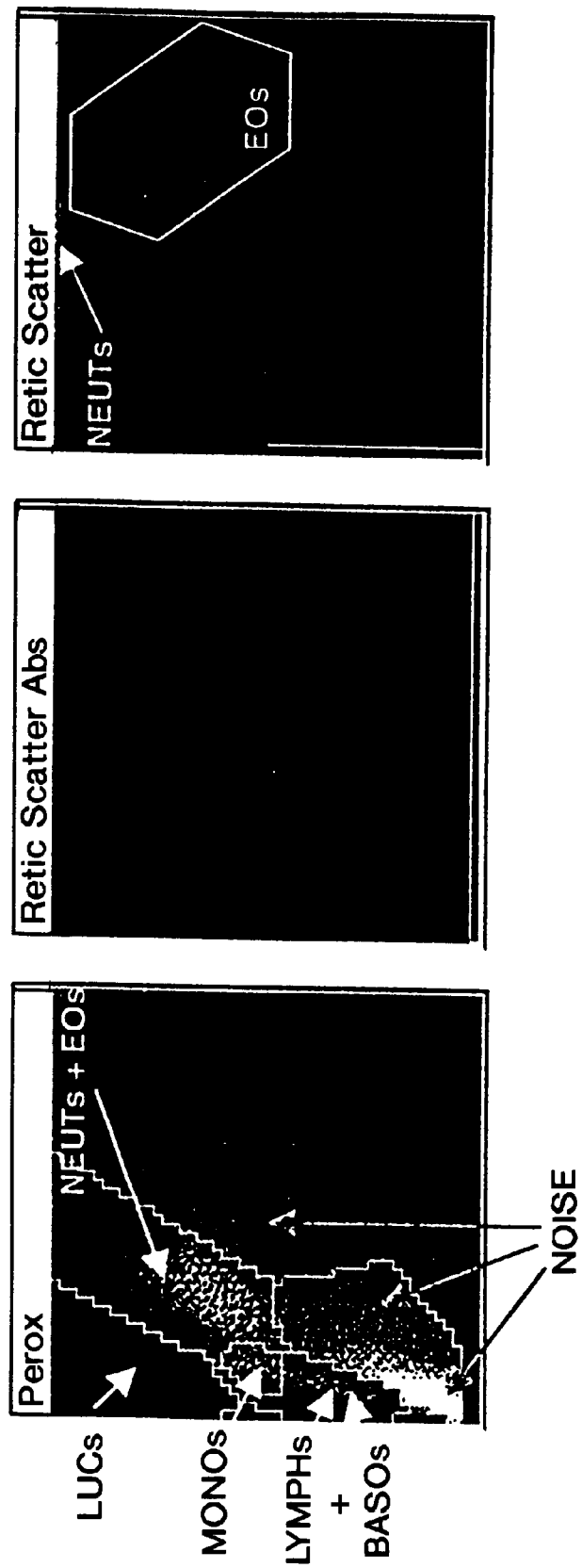

FIG. 11D

| Retic PLT | | |
|---|---|---|
| | % | |
| Neg PLT | 81.3 | 95 × 10³/μL |
| Retic PLT | 18.7 | 22 × 10³/μL |

FIG. 11E

| Platelet | | |
|---|---|---|
| PLT: | 117 | × 10³ cells/μL |
| MPV: | 15.7 | fL |
| PDW: | 78.8 | % |
| PCT: | 0.18 | % |
| MPC: | 26.1 | g/dL |
| PCDW: | 4.0 | g/dL |
| MPM: | 3.81 | pg |
| PMDW: | 2.51 | pg |

US 6,524,858 B1

SINGLE CHANNEL, SINGLE DILUTION DETECTION METHOD FOR THE IDENTIFICATION AND QUANTIFICATION OF BLOOD CELLS AND PLATELETS IN A WHOLE BLOOD SAMPLE USING AN AUTOMATED HEMATOLOGY ANALYZER

This application claims priority to provisional patent application U.S. Serial No. 60/127,209, filed Mar. 31, 1999.

FIELD OF THE INVENTION

The present invention relates generally to an economical single channel method and system for detecting, identifying and quantifying different blood cell types, including platelets, in a mammalian blood sample, including human and non-human whole blood cell samples. Hemoglobin analysis is also provided by the method and system of the present invention. The method and system of the invention are particularly economical and useful for automated hematology analyzers utilizing flow cytometry systems.

BACKGROUND OF THE INVENTION

The detection, identification and quantification of cellular and particulate blood components in a whole blood sample are necessary and customary parameters of blood sample analysis using hematology analyzers involving flow cytometry. A number of semi-automated and automated hematology analyzers can perform blood sample analyses; however, advancements in the technology of hematology analyzers and systems to afford further refinement, economy and accuracy to blood sample analysis advance and improve the ability to distinguish the various blood cell types and perform the necessary blood component analyses on whole blood samples.

Examples of automated hematology analyzers suitable for distinguishing and quantifying red blood cells, including mature red blood cells (RBCs) and reticulocytes, white blood cells (WBCs), including neutrophils, lymphocytes, monocytes, eosinophils and basophils; platelets; and hemoglobin include, but are not limited to the Bayer (formerly Technicon) H*™ Systems series of hematology analyzers (including H*3™ and H*Next™ Systems) and the ADVIA® 120 Hematology System, which are developed and sold by the assignee hereof. The Bayer ADVIA® 120 System is a quantitative multi-channel, multi-dilution automated hematology analyzer that provides red blood cell and platelet analyses, as well as leukocyte (i.e., white blood cell) and reticulocyte analysis for in vitro diagnostic use in clinical laboratories.

Prior to the present invention, the use of hematology analyzers such as those provided above, required separate channels, reagents and channel detection optics for measuring, detecting and distinguishing among the mature red blood cells, reticulocytes, platelets and white blood cells, including neutrophils, lymphocytes and basophils, monocytes and eosinophils in a blood sample. For example, in previous methods and systems, one channel of a hematology analyzer is devoted to the analysis of red blood cells and platelets, a second channel is devoted to the analysis of reticulocytes; a third channel is devoted to the analysis of white blood cells; a fourth channel is devoted to basophil analysis; and a fifth channel is devoted to hemoglobin analysis. Correlated with the use of the different channels in an analyzer is the use of a number of different reagents, e.g., on the order of about five to eight distinct reagents, for diluting a number of aliquots of blood to elucidate the various cell types from one another.

In contrast to prior methods, the present invention provides a single dilution, single measurement channel method, e.g., approximately equivalent to the reticulocyte channel of an automated hematology analyzer and requiring only two reagents, i.e., an aqueous organic dye-containing reagent, preferably a cationic dye, and a sheath/rinse reagent, to discriminate among and measure the parameters of the various types of cells in the red and white blood cell groups, as well as platelets, in a mammalian whole blood sample, and to provide information on hemoglobin in the same sample. More specifically, the method of the present invention provides CBC/Diff/Retic determinations in a single measurement channel, including so-called reticulated platelet counts and percentages. The term "CBC" in the CBC/Diff/Retic determinations is defined as the complete blood count and includes determinations of the following: WBC (white blood cell count; $10^3/\mu l$), RBC (red blood cell count; $10^6/\mu l$), pLT (platelet count; $10^3/\mu l$), HGB (hemoglobin concentration; g/dl), HCT (hematocrit; %), MCV (mean cell volume; fl), MCH (mean cell hemoglobin; pg), MCHC (mean cell hemoglobin concentration; g/dl), RDW (red blood cell volume distribution width; %), HDW (cellular hemoglobin concentration distribution width; g/dl, which is a measure of the variability of cellular hemoglobin concentration within a sample), CHDW (distribution width associated with MCH, wherein (V×hemoglobin concentration= cellular hemoglobin mass), MPV (mean platelet volume), MPC (mean platelet component concentration, g/dl), MPM (mean platelet dry mass), %Neutrophils, [%Lymphocytes+ %Basophils], %Monocytes, %Eosinophils, Absolute Reticulocyte Count ($10^9/l$), %Reticulocytes, Reticulocyte MCV, Reticulocyte MCH and Reticulocyte MCHC, as well as absolute and percentage reticulated platelets.

The term "Diff" in the CBC/Diff/Retic determinations is defined as the white blood cell differential which includes determinations of % (percent) neutrophils, [%lymphocytes+ %basophils], %monocytes and %eosinophils, as well as MNV (mean neutrophil volume), MNC (mean neutrophil component concentration, g/dl), MNM (mean neutrophil dry mass MLV (mean lymphocyte+basophil volume), MLC (mean lymphocyte+basophil component concentration, g/dl), MLM (mean lymphocyte+basophil dry mass MMV (mean monocyte volume), MMC (mean monocyte component concentration, g/dl), MMM (mean monocyte dry mass) MEV (mean eosinophil volume), MEC (mean eosinophil component concentration, g/dl), and MEM (mean eosinophil dry mass).

The term "Retic" in the CBC/Diff/Retic determinations is defined as reticulocytes and includes the absolute reticulocyte count, including %Reticulocytes; Reticulocyte MCV; Reticulocyte MCH and Reticulocyte MCHC. It also includes Reticulated Platelets and the absolute reticulated platelet count and %reticulated platelets.

SUMMARY OF THE INVENTION

It is an object of the present invention to provide a method and system involving a single channel for the detection and measurement of the various types of red and white blood cells, including platelets, in a whole blood sample. Both human and non-human mammalian blood samples are analyzable by the present invention.

In accordance with the method of the present invention, at least three signals are collected and used to determine information about each cell that passes through the flow cell detector of a hematology analyzer substantially one cell at al time. The signals include two scatter signals and either one absorption signal (i.e., scatter/scatter/absorption) or one fluorescence signal (i.e., scatter/scatter/fluorescence). In its simplest aspect, only three signals are needed in the present single channel, single dilution method to count and distinguish from each other all of the platelets, red blood cell types and white blood cell types in a human or non-human mammalian blood sample, including a whole blood sample, based on either the scatter/scatter/absorption or the scatter/scatter/fluorescence pattern. Also according to the new single channel measurement method provided herein, a hematology analyzer may be designed, or adapted, so that it is physically streamlined in terms of space and volume to carry out the analysis of red and white blood cells and platelets, compared with prior analyzers that perform similar functions.

It is another object of the present invention to provide the following parameters and determinations of a complete blood count, i.e., a CBC/Diff/Retic, by the practice of the present single measurement channel method, wherein the CBC includes: WBC (white blood cell count; $10^3/\mu l$), RBC (red blood cell count; $10^6/\mu l$), PLT (platelet count; $10^3/\mu l$), HGB (hemoglobin concentration; g/dl), HCT (hematocrit; %), MCV (mean cell volume; fl), MCH (mean cell hemoglobin; pg), MCHC (mean cell hemoglobin concentration; g/dl), RDW (red blood cell volume distribution width; %), HDW (cellular hemoglobin concentration distribution width; g/dl), CHDW (distribution width associated with MCH, wherein (V×hemoglobin concentration=cellular hemoglobin mass), MPV (mean platelet volume), MPC (mean platelet component concentration, g/dl), MPM (mean platelet dry mass). DIFF includes %Neutrophils, [%Lymphocytes+%Basophils], %Monocytes, %Eosinophils, MNV, MLV, MMV, MEV, MNC, MLC, MMC, MEC, MNM, MLM, MMM, MEM; Retic includes Absolute Reticulocyte Count ($10^9/\mu l$), %Reticulocytes, Reticulocyte MCV, Reticulocyte MCH and Reticulocyte MCHC, as well as absolute reticulated platelet count and %reticulated platelets. HGB is computed as RBC×MCV×MCHC/1000.

It is another object of the present invention to provide a simpler and more convenient method and system for discriminating among the various types of red and white blood cells in a sample, because practice of the method requires only a single reaction chamber of an analyzer and a single dilution step to provide complete blood analysis parameters and values as enumerated above. In addition, the method comprises merely two reagents to achieve the CBC/Diff/Retic blood analysis parameters, namely, 1) a blood diluent reagent composition, preferably an "autoretic" or "retic" reagent (e.g., Bayer ADVIA® Autoreticulocyte Reagent), comprising an organic dye compound, preferably, an organic cationic dye compound, for sample analysis, and 2) a sheath/rinse reagent (e.g., Bayer ADVIA® Universal Rinse Reagent as described in U.S. Pat. No. 5,888,742 to M. Malin et al., the contents of which are hereby incorporated herein by reference) to perform and achieve the detection and quantification results that are afforded by the invention. The term "autoretic" or "retic" reagent as used herein is a shorthand nomenclature referring to a reagent previously used only in the reticulocyte channel of an automated hematology analyzer to identify, distinguish and measure only the red blood cell and reticulocyte populations in a blood sample. A significant advantage of the present single channel method of the present invention is that a single channel cycle is used in conjunction with a single dilution of the blood sample in the diluent reagent. Using only a single blood diluent mixed with a blood sample aliquot, the sample can be analyzed and a complete CBC, DIFF and reticulocyte analysis can be achieved.

Another object of the present invention is to provide a multispecies analysis method and system such that the blood cells of other species can be distinguished and analyzed using the single channel, single dilution method and system to gather and process three optical signals to distinguish white blood cells from all other blood cells, to perform CBC/DIFF/Retic analyses, including reticulated platelet analyses and white blood cell indices for other species.

Further objects and advantages afforded by the invention will be apparent from the detailed description hereinbelow.

DESCRIPTION OF THE DRAWINGS

The appended drawings of the figures are presented to further describe the invention and to assist in its understanding through clarification of its various aspects.

FIGS. 1A–1C show the sum of ten aspirations of a normal human whole blood sample diluted 625-fold in Bayer Autoreticulocyte reagent and analyzed on an ADVIA® 120 Hematology System (Bayer Corporation, Tarrytown, N.Y.), and for which approximately 500,000 total blood cells have been analyzed, as described in Example 1. Included in FIGS. 1A–C are an associated Peroxidase Channel cytogram provided as a control showing distinct cell regions on the cytogram (FIG. 1A); the ungated reticulocyte channel scatter/absorption cytogram (FIG. 1B); the ungated reticulocyte channel scatter/scatter cytogram (FIG. 1C), and the reported WBC parameters or WBC Differential (i.e., WBC count; %Neut. (neutrophils); %Lymph (lymphocytes); %Mono (monocytes); %Eos. (eosinophils); %Baso (basophils); LUC (large unstained lymphocytes); LI (lobularity index); and MPXI (mean peroxidase activity index) averaged over the ten aspirations. The cell types are labeled on the reticulocyte cytograms, where "PLT" refers to platelets; "Monos" refers to monocytes; "Lymphs" refers to lymphocytes; "WBC" refers to white blood cells (also called leukocytes); "Retics" refers to reticulocytes; and "RBC" refers to red blood cells.

FIGS. 2A–2C show the sum of ten aspirations of a normal human whole blood sample diluted 625-fold in Bayer Autoreticulocyte reagent and analyzed on an ADVIA® 120 Hematology System (Bayer Corporation, Tarrytown, N.Y.). FIGS. 2A–C include the same reticulocyte cytograms as described in FIGS. 1A–1C, but the FIGS. 2A–2C results are gated to include only cells whose absorption values exceed absorption channel 80 on the absorption axis ("x axis") of the scatter/absorption cytogram, where the absorption values range from 0 to 99. Thus, in FIG. 2C in the gated reticulocyte scatter cytogram, the regions where the neutrophils (Neuts), monocytes and eosinophils (EOS) fall out in the blood sample analysis can be observed. The WBC Differential for FIGS. 2A–2C are those shown for FIGS. 1A–1C.

As described above for FIGS. 1A–C, FIG. 3A shows the control peroxidase channel analysis; FIG. 3B shows the reticulocyte channel scatter/absorption cytogram, while FIG. 3C shows the reticulocyte channel scatter/scatter cytogram. Also shown are the reported WBC Differential parameters as defined above.

FIGS. 4A–4C to 9A–9C depict the results of three separate analyses of feline whole blood samples. The results of three separate experiments are presented in FIGS. 4A–4C through 9A–9C. The figures include reference peroxidase channel cytograms (FIGS. 4A, 5A, 6A, 7A, 8A and 9A), as well as ungated scatter/absorption cytograms (FIGS. 4B, 5B and 6B) and ungated scatter/scatter cytograms (FIGS. 4C, 5C and 6C) and their gated counterparts (FIGS. 7B, 8B and 9B; and 7C, 8C and 9C, respectively). It is to be noted that, in contrast to the human blood sample Peroxidase cytograms, (FIGS. 1A and 2A, for example), feline Peroxidase cytograms do not display distinct eosinophil clusters. This is due to the peroxidase negativity of feline eosinophils. However, the gated scatter/scatter cytograms show distinct eosinophil clusters for eosinophil percentages of 2% to 16% in the three samples represented.

FIGS. 4A–4C, 5A–5C and 6A–6C depict the cytograms showing the ungated results from the three experiments analyzing different cat whole blood samples. FIGS. 7A–7C, 8A–8C and 9A–9C depict the cytograms showing the gated results that correspond with the ungated cytogram results shown in FIGS. 4A–4C, 5A–5C and 6A–6C, respectively. The ungated scatter/scatter cytograms (FIGS. 4C, 5C, and 6C) include distinct clusters for red cells (including coincidences), platelets, lymphocytes (and monocytes), and some of the polymorphonuclear cells. The ungated scatter/absorption cytograms (FIGS. 4B, 5B and 6B) have distinct clusters for platelets, red cells/reticulocytes/red coincidences, and white cells. The reticulocytes were distinguished from the mature red cells by statistical analysis of the red cell/reticulocyte absorption channel histogram.

The gated scatter/scatter cytograms (FIGS. 7A–7C, 8A–8C and 9A–9C) include cells whose absorption signals appear in the saturation absorption channel (channel 99 of the absorption axis of the scatter/absorption cytogram, where the absorption axis ranges from channel 0 to channel 99). In the gated scatter/scatter cytograms (FIGS. 7C, 8C and 9C), the eosinophil cluster is distinguished from the neutrophil cluster.

The WBC Differential data for FIGS. 4A–4C (ungated) and FIGS. 7A–7C (gated); FIGS. 5A–5C (ungated) and FIGS. 8A–8C (gated); and FIGS. 6A–6C (ungated) and FIGS. 9A–9C (gated) are identical. Only the WBC Differential data for the ungated cytograms are presented. These grouped figures represent the ungated and gated results from 3 different feline blood samples.

Figure 10:
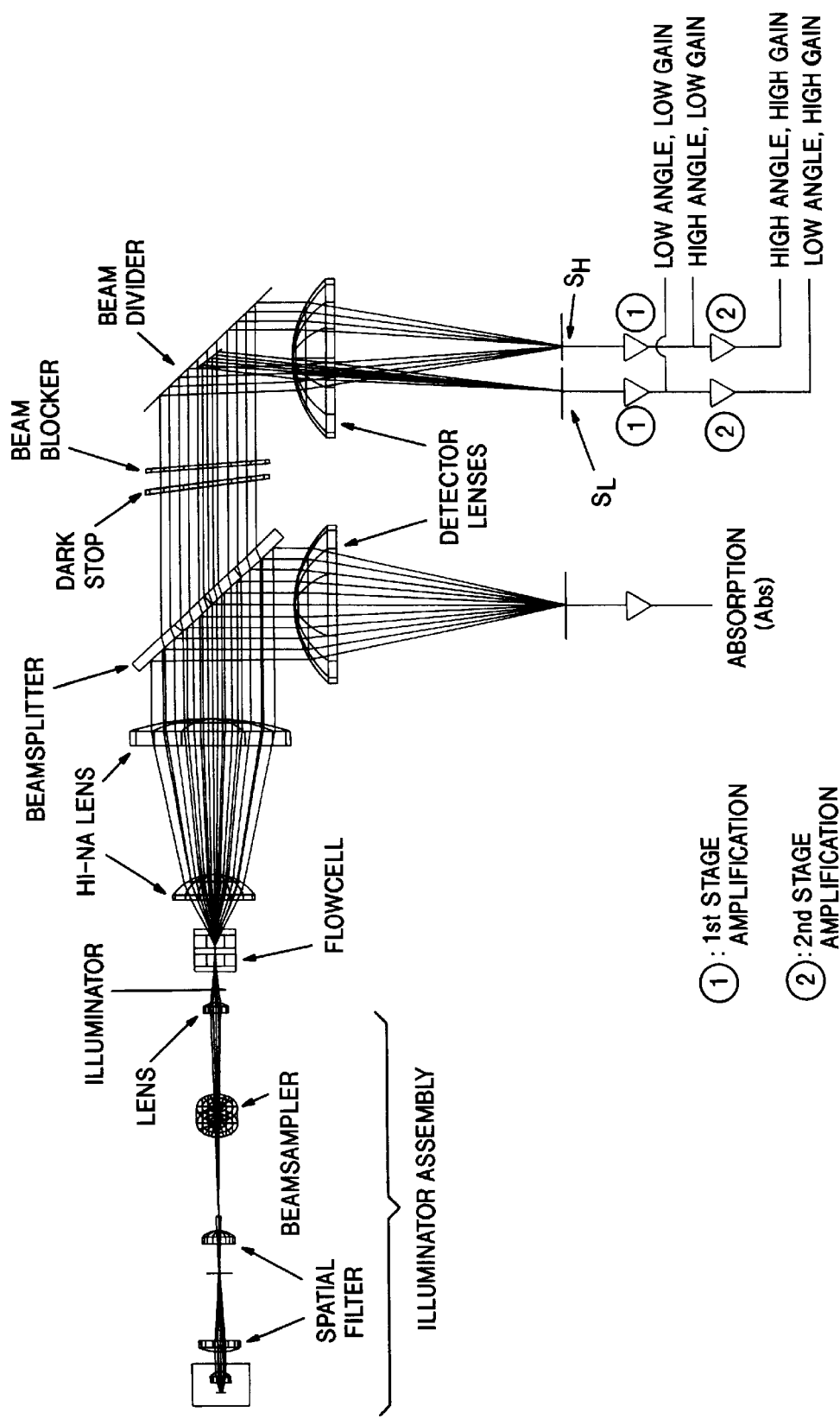

FIG. 10 shows a schematic depiction of the optical design associated with the single channel method of the present invention.

Figure 11A:
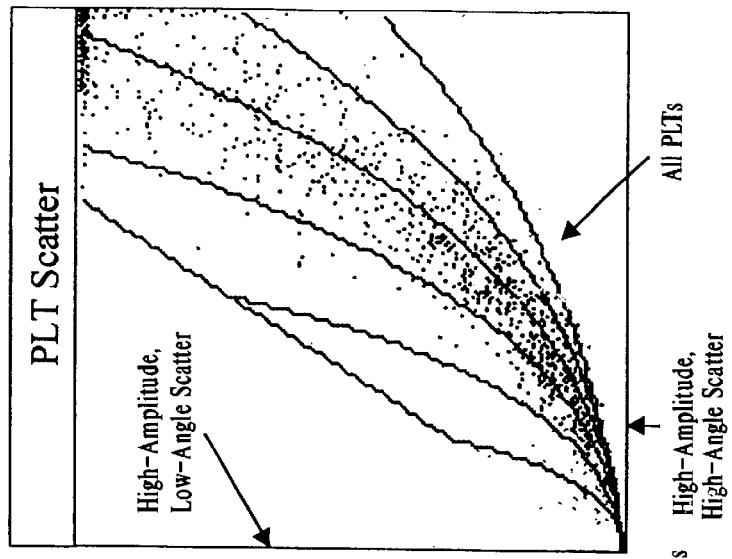
Figure 11B:
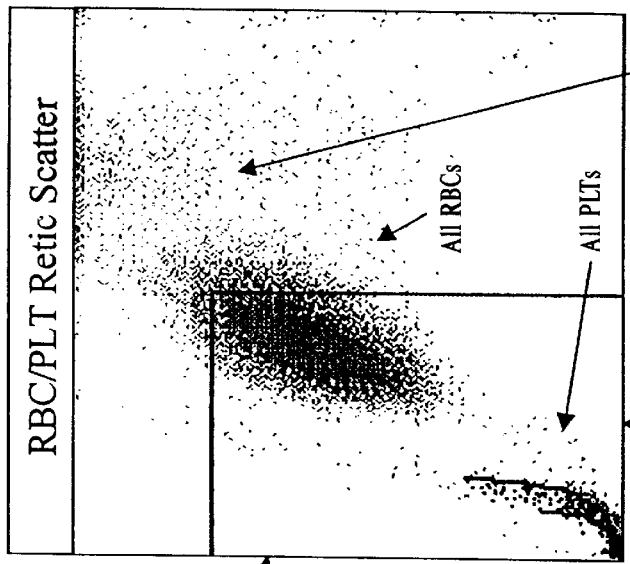
Figure 11C:
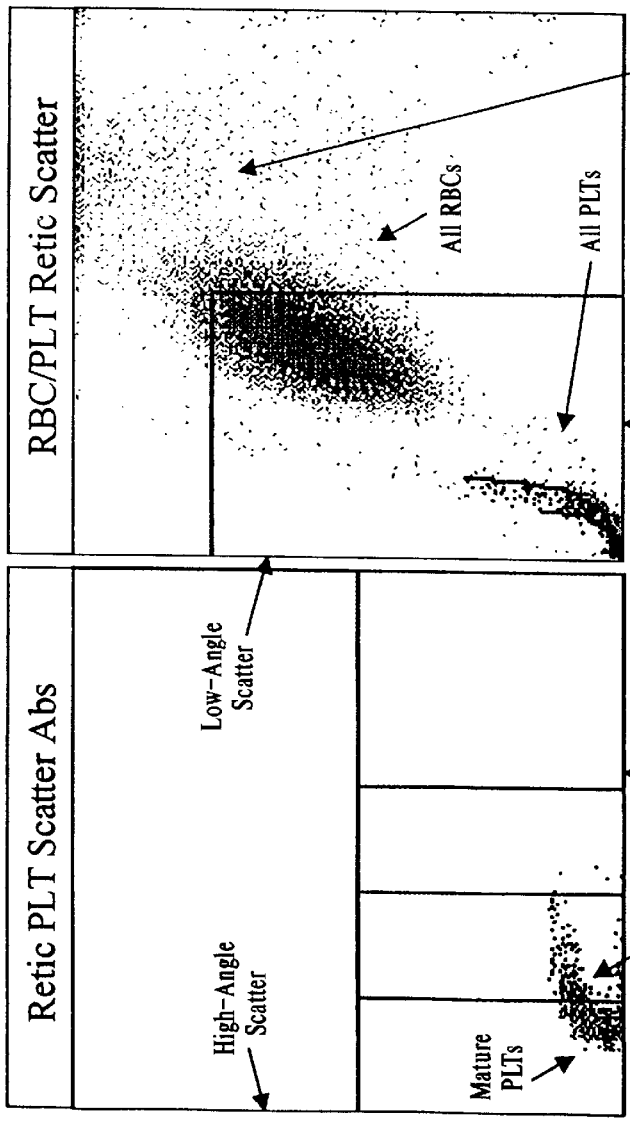

FIGS. 11A–11E show scatter/absorption cytograms resulting from the analysis of reticulated platelets. Reticulated platelets are platelets that are less than approximately 24 hours old in the peripheral blood. They contain distinguishably higher concentrations of nucleic acid than mature platelets. A significant change in their percentage or absolute number signifies a change in thrombopoietic activity. FIG. 11A shows a reticulated platelet high-angle scatter/absorption cytogram; FIG. 11B shows an RBC/PLT Retic low-angle scatter/high-angle scatter cytogram, and FIG. 11C shows a platelet high-amplification, low-angle scatter/high-amplification, high-angle scatter cytogram. Also presented are a reticulated platelet (Retic PLT) parameter table (FIG. 11D) and a platelet (PLT) parameter table (FIG. 11E).

DETAILED DESCRIPTION OF THE INVENTION

The present invention provides a method and system for use with automated hematology analyzers wherein a single channel is used to differentiate, identify and quantify the different blood cells and blood cell components, including platelets, in a whole blood sample. Both human and non-human mammalian blood samples can be analyzed using the present invention.

It has been newly discovered that a single channel, generally known and only used as a reticulocyte analysis channel, of an automated hematology analyzer, such as the Bayer (formerly Technicon) H*™3 Hematology Analyzer and the ADVIA® 120 Hematology Analyzer (Bayer Corporation, Tarrytown, N.Y.), involving flow cytometry analysis of blood samples, can be used to distinguish among all of the red blood cells, white blood cells and platelets in a blood sample, including human and non-human blood samples Current automated analyzers and flow cytometric analyzer systems that can be used, or adapted for use, in practicing the method of the present invention and which are suitable for use with the scatter/scatter and scatter/absorption system operative in and exemplified by the above-mentioned automated Bayer H*3 Hematology Analyzer and the ADVIA® Hematology Analyzer are described in U.S. Pat. No. 5,817,519 to D. Zelmanovic et al., U.S. Pat. Nos. 5,438,003 and 5,350,695 to G. Colella et al., and U.S. Pat. No. 4,735,504 to Tycko, the contents of all of which are herein incorporated by reference. It will be appreciated that other hematology analyzer instruments having suitable hardware and system components may be used, or adapted for use, in accordance with the present invention.

The performance of the method of the present invention involves the use of an aqueous reagent composition, or blood diluent reagent composition (e.g., an autoretic or retic reagent composition such as the ADVIA® 120 Autoretic Reagent sold by Bayer Corporation), comprising an organic dye compound for staining RNA of reticulocytes and the nucleic acid, i.e., DNA and RNA, of white blood cells in a whole blood sample aliquot and which does not precipitate out of the reaction mixture formed by mixing the blood sample aliquot with the diluent reagent, and a buffer or buffer mixture. The buffer or buffer mixture maintains a neutral or an approximately neutral pH of the reagent composition and reaction mixture (i.e., a pH of about 6 to about 9, preferably about 7 to about 8, more preferably about 7.2 to about 7.8, and most preferably about 7.3 to about 7.5), and is preferably isotonic, so as to insure that the cells are substantially isovolumetrically sphered by the surfactant. The blood diluent reagent composition is mixed with an aliquot of a mammalian whole blood sample, preferably anticoagulated, to form an aqueous reagent mixture or reagent solution analyzable in the present method. For optimum platelet determinations, the whole blood sample is anticoagulated, preferably in $K_3$ EDTA.

Examples of other blood diluent reagent compositions that are suitable for use in the present method are described in U.S. Pat. No. 5,411,891 to S. Fan et al. and U.S. Pat. No. 5,438,003 to G Colella et al. and in U.S. Pat. No. 6,114,173 the contents of which are incorporated herein by reference in their entirety.

Nucleic acids (RNA and DNA) are polyanions which can be stained with practically any organic cationic dye. However, both the RNA in reticulocytes and the RNA and DNA (nucleic acids) in white blood cells can be effectively stained with the cationic dyes, including, for example, Brilliant Cresyl Blue (BCG), New Methylene Blue (NMB), Auramine 0 (AuO), Acridine Orange (AO), Thiazole Orange (TO), Oxazine 750, and Pyronine Y (PY). Among these dyes, only a subset can penetrate the cells and nuclei (and therefore stain) rapidly. The rate and degree of staining of reticulocytes depend upon the extracellular concentration of the dye, the rate of penetration of the dye through the cell membrane, and the strength of the specific binding constant between the dye and the cell's RNA and/or DNA. The latter two properties are different, and are not easily predictable for each dye, so that routine trial and error may be necessary to discover useful nucleic acid stains.

Cationic dyes preferred for use in the reagent composition of the present invention include, but are not limited to, the blue absorption dye Oxazine 750 (Exciton, Inc., Dayton, Ohio); or the blue absorption dye New Methylene Blue.

The blood diluent reagent may further include one or more of the following components, at the concentrations noted, with the final osmolality adjusted with sodium chloride or potassium chloride to from about 250 milliosmoles (m Osm) to about 330 milliosmoles: $K/NaHCO_3$ at a concentration of about 5–50 mM; $MgCl_2$ at a concentration of about 0–88 mM; KCl at a concentration of about 4–104 mM; $Na_3PO_4$ at a concentration of about 0–1.5 mM; and $CaCl_2$ at a concentration of about 0–0.6 mM. Preferably, the buffer solution is formulated to maintain the pH of the autoretic reagent composition at between about 7 to about 8, most preferably about 7.4, and, accordingly, may include one or more of the following components, in the concentration ranges given, with the final osmolality of from about 280 m Osm to about 300 m Osm: Tris/TEA at a concentration of about 0–150 mM; $K_2$ Ox/EDTA at a concentration of about 0–121 mM; and KCl/NaCl at a concentration of about 0–155 mM.

The reagent composition may also include certain anions and cations (e.g., alkyl metal chlorides) to facilitate the dye penetration through cell membranes. Nonlimiting examples of anions include bicarbonate, chloride borate, barbital, oxalate (Ox), or ethylenediaminetetraacetic acid (EDTA). It is to be noted that not all anions have been found to be effective in promoting dye penetration across cell membranes. For example, when one or more of the following anions: malate, tartarate, or phosphate was included in the reagent compositions as the only major anions, little, if any, distinction could be made between reticulocytes and erythrocytes. Nonlimiting examples of suitable cations include sodium (e.g., NaCl), potassium (e.g., KCl), trishydroxymethylamino methane (Tris), (Tris[hydroxymethyl]-aminomethane-hydrochloric acid (Tris-HCl), or triethanolamine (TEA).

An antimicrobial compound can also be included in the reagent composition to retard microbial growth. Nonlimiting examples of suitable antimicrobials include Proclin 150 (2-methyl-4-isothiazolin-3-one) and Proclin 300 (5-chloro-2-methyl-4-isothiazolin-3-one) (Rohm & Haas); Germall 115 (N,N'-methylenebis[N'-(1-(hydroxymethyl)-2,5-dioxo-4-imidazolidinyl]urea) (Sutton Laboratories); Dowacil 200 (1-(3-chloroallyl)-3,5,7-triaza-1-azoniaadamantane chloride) (Dow Chemical); and Bronopol 2-bromo-2-nitropropane-1,3-diol ($C_3H_6BrNO_4$), (Angus Chemical Company). Proclin 300 is a preferred antimicrobial for use in the reagent composition employed in the present invention.

In the presence of the above-described buffer systems, the concentration of the Oxazine 750 dye in the reagent composition is in the range of from about 2 µg/ml to about 15 µg/ml. The concentration of the New Methylene Blue dye in the reagent composition is in the range of from about 10 µg/ml to about 100 µg/ml. These concentrations were found to be appropriate for the staining of RNA in the reticulocytes.

The blood diluent reagent composition employed in the present method (e.g., the autoretic reagent) may also contain a sphering agent, in the form of a nonionic or a zwitterionic surfactant to substantially and effectively sphere red blood cells, reticulocytes, white blood cells and platelets in the sample. Zwifterionic surfactants are preferred. It is also to be noted that platelets in the collected blood sample are effectively sphered by virtue of the EDTA present in the collected sample. The surfactant as sphering agent is one which does not substantially lyse the red blood cells (or other blood cell types) in the blood sample undergoing analysis in the single channel, single dilution method according to this invention. That is, the method of the present invention, and the reagent composition used therein, are virtually non-lysing for red blood cells and other blood cells in the blood sample.

Examples of suitable nonionic surfactants include, but are not limited to, the alkylglycosides, such as dodecyl maltoside, more particularly, for example, n-dodecyl-β-D-maltoside, n-tetradecyl-β-D-maltoside and n-tetradecyl-β-D-glucoside.

If a zwitterionic surfactant is employed, it is preferably an alkyl amido betaine or an alkyl betaine, such as lauramidopropyl betaine (LAB), cocoamidopropylbetaine (CAPB), or cocoamidosulfobetaine (CASB). Other preferred sphering agents are N-tetradecyl-N,N-dimethyl-3-ammonio-1-propanesulfonate (TDAPS) and N-dodecyl-N,N-dimethyl-3-ammonio-1-propanesulfonate (DDAPS). Both TDAPS and DDAPS provide the most stable sample preparation.

For effective isovolumetric sphering of the red blood cells, reticulocytes and white blood cells in a blood sample, the concentration of the sphering agent in the reagent composition is generally from about 3.9 µg/ml to about 148 µg/ml. In the case of LAB, the sphering agent is preferably present in the reagent composition in an amount from about 12 µg/ml to about 87.5 µg/ml; for TDAPS as sphering agent, TDAPS is preferably present in the reagent composition in an amount of from about 3.9 µg/ml to about 11.8 µg/ml; for DDAPS as sphering agent, DDAPS is preferably present in the reagent composition in an amount of from about 49.3 µg/ml to about 148 µg/ml; for CAPB as sphering agent, CAPB is preferably present in the reagent composition in an amount of from about 8.8 µg/ml to about 17.5 µg/ml; and for CASB as sphering agent, CASB is preferably present in the reagent composition in an amount of from about 12.5 µg/ml to about 15 µg/ml.

A preferred diluent reagent composition (e.g., autoretic reagent composition) especially useful in the single channel method of the present invention contains a cationic dye, as described above, at an increased cationic dye concentration, a sphering agent, as described above, and a reduced reagent pH, for example, as described in patent application U.S. Ser. No. 08/833,033, filed Apr. 3, 1997. The reagent may also contain one or more nucleophiles, such as azides ($N_3^-$). for example, sodium azide; or cyanate ($OCN^-$) ion, for example, sodium cyanate. The pH of the preferred autoretic reagent composition is about 7.2 to 7.8, preferably 7.3 to 7.5, and more preferably, 7.4. The osmolality of the reagent composition is about 250 m Osm to about 320 m Osm, preferably about 287 m Osm to about 297 m Osm, and more preferably about 292 +/−5 m Osm. In this preferred autoretic reagent solution, the concentration of cationic dye, e.g., Oxazine 750, is from about 6 μg/ml to about 20 μg/ml, preferably from about 6.5 μg/ml to about 19.5 μg/ml, and more preferably from about 9 μg/ml to about 10.5 μg/ml.

Typically, the cationic dye in the blood diluent reagent, after mixing with a blood sample, stains the RNA of reticulocytes and the DNA and RNA in the nuclei of nucleated cells in the sample, including white blood cells. This staining allows the identification of these blood cell types in the reticulocyte channel from other blood cell types which, until the present invention, were required to be identified and distinguished by using several additional and distinct channels of the analyzer, for example, the Basophil (Baso) channel and the Peroxidase (Perox.) channel. In addition, the blood diluent reagent does not substantially lyse any of the blood cell types, including red blood cells and platelets, undergoing analysis in the method. Therefore, each measurement cycle of the method includes relative counts of red blood cells, reticulocytes, platelets, reticulated platelets and white blood cells.

The discovery that the above-described autoretic reagent composition could stain not only the RNA of reticulocytes but also the DNA and RNA of white blood cells so as to distinguish them from other cells in the single channel method, provides a significant advantage of the present method over other WBC differentiation methods. For example, unlike standard methods of WBC evaluation, there is no potential for damage to selected WBC types as a result of RBC lysis, which might have an adverse impact on the WBC count or on differential accuracy. Another significant advantage is that the relative cell counts in a blood sample all derive from a single dilution step, which simplifies calibration and upholds accuracy. Yet another advantage, the use of and need for only one blood diluent reagent used in a single channel of the analyzer eliminates the need for multiple, different reagents and/or separate solutions used in separate channels of the analyzer. An additional advantage in this regard is that there is no need to subdivide the blood aliquot by mechanical or other means, such as via a shear valve, thus further simplifying the instrument design.

Included among the reported parameters obtained by the practice of the single channel method of the present invention are the following: WBC (white blood cell count; $10^3$/μl), RBC (red blood cell count; $10^6$/μl), PLT (platelet count; $10^3$/μl), HGB (hemoglobin concentration; g/dl), HCT (hematocrit; %), MCV (mean cell volume; fl), MCH (mean cell hemoglobin; pg), MCHC (mean cell hemoglobin concentration; g/dl), RDW (red blood cell volume distribution width; %), HDW (cellular hemoglobin concentration distribution width; g/dl), MPV (mean platelet volume), MPC (mean platelet component concentration, g/dl), MPM (mean platelet dry mass), %Neutrophils, [%Lymphocytes+ %Basophils], %Monocytes, %Eosinophils, Absolute Reticulocyte Count ($10^9$/μl), %Reticulocytes, Reticulocyte MCV, Reticulocyte MCH and Reticulocyte MCHC. HGB is computed as RBC×MCV×MCHC/1000. Also included are absolute and percent reticulated platelet count, as well as mean cell volume, mean component concentration (or cell density) and mean dry mass for white blood cell types.

The above information and parameters values provided by the single channel method as described herein are assigned as follows:

RBC count ($10^6$/μL) is based on the number of signals identified as cells by the high-gain, high-angle scattering detector. The number of cells detected is subsequently partitioned into RBCs and non-RBCs according to the regions occupied by these cells in low-gain scatter/scatter space, as further described in the description and examples herein.

PLT count ($10^3$/μL) is based on the number of signals identified as cells, as described above for RBC count, except that cells are partitioned into PLTs and non-PLTs according to the regions they occupy in high-gain scatter/scatter space, rather than low-gain scatter/scatter space, as further described in the description and examples herein.

MCV (fL) is determined by converting the pair of low-gain scattering intensity values for each cell identified as an RBC into the corresponding pair of cell volume and hemoglobin concentration values by reference to conversion tables derived from Mie Scattering Theory calculations. The sum of cell volume values is divided by the sum of cells analyzed to arrive at MCHC (g/dL) is determined by summing the cellular hemoglobin concentration values associated with each cell, based on the above-described Mie Scattering conversion tables, and then dividing the sum by the sum of cells analyzed.

MCH (pg)=MCV×MCHC/100.

HGB (g/dL)=RBC×MCV×MCHC/1000.

HCT(%)=RBC×MCV/10.

RDW (%)=Standard Deviation of the red blood cell volume values/MCV.

HDW (g dL)=Standard Deviation of the cellular hemoglobin concentration values.

CHDW (pg)=Standard Deviation of the cellular hemoglobin content values (which go into making MCH).

MPV (fL) is determined by converting the pair of high-gain scattering intensity values for each cell identified as a PLT into the corresponding pair of cell volume and platelet component concentration values by reference to a conversion table derived from Mie Scattering Theory calculations. The sum of cell volume values is divided by the sum of cells analyzed to arrive at MPV.

MPC (g/dL) is determined by summing the platelet component concentration values associated with each cell, based on the above-described conversion tables, and then dividing this sum by the sum of cells analyzed.

MPM (pg)=MPV×MPC/100.

Absolute Neutrophil Counts ($10^3$/μL) are determined by the number of cells identified as neutrophils by their coordinates in scatter/scatter/absorption space or scatter/scatter/ fluorescence space, as further described in the description and examples herein.

Absolute Lymphocyte+Basophil Counts ($10^3$/μL) are determined by the number of cells identified as lymphocytes+ basophils by their coordinates in scatter/scatter/absorption space, or scatter/scatter fluorescence space, as further described in the description and examples herein.

Absolute Monocyte Counts ($10^3$/μL) are determined by the number of cells identified as monocytes by their coordinates in scatter/scatter/absorption space or scatter/scatter/ fluorescence space, as further described in the description and examples herein.

Absolute Eosinophil Counts ($10^3/\mu L$) are determined by the number of cells identified as eosinophils by their coordinates in scatter/scatter/absorption space scatter/scatter/fluorescence space, as further described in the description and examples herein.

WBC count ($10^3/\mu L$) Absolute Neutrophil count+Absolute [Lymphocyte+Basophil]count+Absolute Monocyte count+Absolute Eosinophil count.

Absolute Reticulocyte Count ($10^9/\mu L$) is determined by the number of cells that are first identified as RBCs in the low-gain scatter/scatter cytogram and then distinguished from mature RBCs based on their coordinates in scatter/absorption or scatter/fluorescence space, as further described in the description and examples herein.

% Reticulocytes (%)=Absolute Reticulocyte Count/RBC.

Reticulocyte MCV (fL) is the mean cell volume, as determined above, of those cells designated as reticulocytes according to the absolute reticulocyte count.

Reticulocyte MCHC (g/dL) is the mean cellular hemoglobin concentration, as determined above, of those cells designated as reticulocytes.

Reticulocyte MCH (pg) is the mean cellular hemoglobin, as determined above, of those cells designated as reticulocytes.

Absolute Reticulated Platelet Count ($10^3$/L) is determined by counting the number of particles identified as platelets, as described above, and then distinguishing reticulated platelets from mature platelets based on their coordinates in scatter/absorption or fluorescence space.

Mean Neutrophil Volume (fL) is determined by converting the pair of scattering intensity values for each particle identified as a neutrophil into the corresponding pair of cell volume and refractive index values by reference to a Mie Scattering Theory conversion table. The sum of the volume values is divided by the sum of cells analyzed to arrive at Mean Neutrophil Volume.

Mean Lymphocyte+Basophil Volume (fL) is determined by converting the pair of scattering intensity values for each particle identified as a lymphocyte or as a basophil into the corresponding pair of cell volume and refractive index values by reference to a Mie Scattering Theory conversion table. The sum of the volume values is divided by the sum of cells analyzed to arrive at Mean Lymphocyte+Basophil Volume.

Mean Monocyte Volume (fL) is determined by converting the pair of scattering intensity values for each particle identified as a monocyte into the corresponding pair of cell volume and refractive index values by reference to a Mie Scattering Theory conversion table. The sum of the volume values is divided by the sum of cells analyzed to arrive at Mean Monocyte Volume.

Mean Eosinophil Volume (fL) is determined by converting the pair of scattering intensity values for each particle identified as an eosinophil into the corresponding pair of cell volume and refractive index values by reference to a Mie Scattering Theory conversion table. The sum of the volume values is divided by the sum of cells analyzed to arrive at Mean Eosinophil Volume.

Mean Neutrophil Component Concentration (g/dL) is determined by summing the neutrophil component concentration values associated with each cell, based on the above-described Mie Scattering Theory conversion table, and then dividing this sum by the sum of cells analyzed.

Mean Lymphocyte+Basophil Component Concentration (g/dL) is determined by summing the lymphocyte and basophil component concentration values associated with each cell, based on the above-described conversion table, and then dividing this sum by the sum of cells analyzed.

Mean Monocyte Component Concentration (g/dL) is determined by summing the monocyte component concentration values associated with each cell, based on the above-described conversion tables, and then dividing this sum by the sum of cells analyzed.

Mean Eosinophil Component Concentration (g/dL) is determined by summing the eosinophil component concentration values associated with each cell, based on the above-described conversion tables, and then dividing this sum by the sum of cells analyzed.

Mean Neutrophil Dry Mass (pg)=Mean Neutrophil Volume×Mean Neutrophil Component Concentration.

Mean Lymphocyte+Basophil Dry Mass (pg)=Mean Lymphocyte+Basophil Volume×Mean Lymphocyte+Basophil Component Concentration.

Mean Monocyte Dry Mass (pg)=Mean Monocyte Volume×Mean Monocyte Component Concentration.

Mean Eosinophil Dry Mass (pg)=Mean Eosinophil Volume×Mean Eosinophil Component Concentration.

A second reagent is preferably employed in the single measurement channel method of the present invention. This is a sheath reagent or rinse reagent composition (i.e., a sheath/rinse reagent), such as that described in U.S. Pat. No. 5,888,752 to M. Malin et al., the contents of which are incorporated by reference herein. Other similar reagents may be used, such as an RBC/sheath reagent, as described in U.S. Pat. No. 5,817,519 to D. Zelmanovic et al., to cleanse the system components and hardware during and/or following blood sample analysis. When the sheath/rinse reagent is used, it acts as a sheathing agent for the optical flow cell measurements, as well as a rinsing agent or cleansing agent for components, hydraulic lines and tubing of the analyzer, which can also be used between different sample aspirations. Sheath reagents, such as the above-mentioned sheath/rinse reagent are passive reagents which do not interact with blood cells directly, but instead, can surround and center a stream in the flowcell, or rinse the flowcells and various components of a hematology analyzer system without affecting blood sample analysis.

The present invention distinguishes among the various blood cell types in a whole blood sample based on the positions of the particles (i.e., cells) in a three-dimensional measurement space comprised of low-angle scattering intensity, high-angle scattering intensity, and either light absorption or fluorescence intensity. Tables 1 to 3 present the channel ranges occupied by each particle type within each of the three dimensions, for each of the signal dynamic ranges. The values shown in the tables are channel numbers, with the total range being from 0 to 99. Tables 1 to 3 are based on the results determined for human blood samples, and light absorption is used as the third measurement dimension.

TABLE 1

Platelet (PLT) Dynamic Range
PARAMETER

| CELL TYPE | LOW-ANGLE SCATTER | HIGH-ANGLE SCATTER | LIGHT ABSORPTION |
|---|---|---|---|
| PLT | 0–99 | 0–99 | |
| Reticulated PLT | 0–99 | 0–99 | 8–15 |
| All Others | >99 | >99 | Various |

TABLE 2

Red Blood Cell (RBC) Dynamic Range
PARAMETER

| CELL TYPE | LOW-ANGLE SCATTER | HIGH-ANGLE SCATTER | LIGHT ABSORPTION |
| --- | --- | --- | --- |
| RBC | 20–60 | 20–60 | 0–20 |
| Reticulocyte | 40–60 | 15–40 | 21–90 |
| PLT | <3 | <8 | <7 |
| Reticulated PLT | <3 | <8 | 8–15 |
| Neutrophil | >99 | 60–80 | 99 |
| Lymphocyte/Basophil | 60–80 | 10–20 | 50–90 |
| Monocyte | 90–99 | 15–25 | 80–95 |
| Eosinophil | 60–90 | 60–90 | 99 |
| RBC Coincidence | 60–99 | 60–99 | 20–60 |

TABLE 3

White Blood Cell (WBC) Dynamic Range
PARAMETER

| CELL TYPE | LOW-ANGLE SCATTER | HIGH-ANGLE SCATTER | LIGHT ABSORPTION |
| --- | --- | --- | --- |
| Neutrophil | 60–80 | 40–55 | 99 |
| Lymphocyte/Basophil | 4055 | 7–14 | 50–90 |
| Monocyte | 60–80 | 10–17 | 80–95 |
| Eosinophil | 40–60 | 40–60 | 99 |
| RBC | 13–40 | 23–40 | <20 |
| Reticulocyte | 27–40 | 10–27 | 21–90 |
| RBC Coincidence | 40–60 | 40–65 | 20–60 |
| PLT | <2 | <5 | <7 |
| Reticulated PLT | <2 | <5 | 8–15 |

As Table 1 indicates, each particle type occupies a unique region in this three-dimensional signal space. The different dynamic ranges are needed in order to provide adequate signal resolution for the small-signal platelets and reticulated platelets on the one hand, and to bring neutrophils and eosinophils, that have saturation-level scattering signals, back into viewing range, on the other hand. Each dynamic range is established by applying specific amplification factors to the pair of scattering signals. In this embodiment, a single absorption channel amplification factor was employed. However, it should be understood that this need not be the case, and if necessary, the absorption/fluorescence signal amplification factors may be adjusted. If sufficiently high resolution analog to digital (A/D) signal conversion, e.g., 14-bit, is used along with sufficiently large memory (RAM), e.g., 10 megabytes, then separate amplifiers are not required.

Beginning with the amplification factors suitable for platelets, which require the highest amplification since they produce the smallest signals as a group, Table 1 shows that platelets and reticulated platelets are distinguished from all other blood cell types because all other cells have signals greater than the maximum signal allowable for platelets. Reticulated platelets are distinguished from platelets based on their absorption of light (or fluorescence) due to uptake of dye.

At the next lower amplification plateau, red blood cells/reticulocytes are distinguished from platelets/reticulated platelets because of their increased scattering intensity. Red blood cells/reticulocytes are distinguished from white blood cells because of the unique position of the white cells in scatter/scatter/absorption or fluorescence space. Lymphocytes/basophils are distinguished from other cell types because they occupy unique position in scatter/scatter space and also because they have higher absorption (or fluorescence) signals. Monocytes may be partially obscured in scatter/scatter space by coincidence signals, but are resolved in the absorption (or fluorescence) dimension by their larger signals. Neutrophils and eosinophils are completely obscured by coincidence signals, but they too are resolved by their large absorption (or fluorescence) signals. Reticulocytes are distinguished from red blood cells based on their absorption of light (or fluorescence) due to uptake of dye.

At the lowest amplification level, white blood cells are distinguished from red blood cells/reticulocytes and platelets/reticulated platelets as described above. The low amplification is needed to remove the neutrophil, eosinophil, and some of the monocyte scatter/scatter signals out of saturation, so that all the white blood cell types may be mutually distinguished based on their unique positions in scatter/scatter/absorption (or fluorescence) space.

It can be understood from the description above that the various particle types can be uniquely determined in this three signal-space without reference to scattering theory. However, application of Mie scattering theory to the clusters of particle types provides important additional information about these particles. For each category of particles, i.e., platelets, red cells, and white cells; the theory may be applied to convert the pair of scattering signals or the trio of scatter/scatter/absorption or fluorescence signals into volume and refractive index values for each of the particles within the respective clusters. This information can be used to produce mean values for volume, cell component concentration (or density), and dry mass.

In the case of red blood cells, this allows the method of the invention to provide MCV (mean red blood cell volume), (for example, see U.S. Pat. No. 4,735,504 to Tycko). Since hemoglobin concentration is linearly related to cell density, which is, in turn, linearly related to refractive index, MCHC (mean cellular hemoglobin concentration) can also be obtained. Further, since the method of the invention also provides a RBC counts, the product of RBC, MCV, and MCHC can be used to provide a value for HGB, which is the overall concentration of hemoglobin in the blood (g/dL). In addition, the product of MCV and MCHC provides MCH (mean cellular hemoglobin, pg). The same information can be obtained for reticulocytes.

In the case of platelets, MPV (mean platelet volume) and MPC (mean platelet component concentration) may be obtained analogously to MCV and MCHC. The product of MPV and MPC provides MPM (mean platelet dry mass, pg). Again, the same information may be obtained for reticulated platelets. For white blood cells, mean cell volumes, component concentrations, and mean dry mass values may be obtained for each of the white cell clusters, as newly provided by the present invention.

As a specific, yet nonlimiting example, reticulocyte channel scatter/scatter cytograms, scatter/absorption cytograms, and gated scatter/scatter cytograms are presented for feline whole blood samples analyzed by the above method. Although the particle types are distinguished in three-dimensional space, the examples are presented as projections onto two-dimensional space, for ease of visualization. (See Example 3 and FIGS. 4A–4C through 9A–9C). The gated scatter/scatter cytograms include cells whose absorption signals appear in the saturation absorption channel (channel 99) as determined on the absorption axis of the scatter/absorption cytogram. The ungated scatter/scatter cytograms include distinct clusters for red cells (including coincidences), platelets, lymphocytes+basophils and monocytes, and some of the polymorphonuclear cells. The ungated scatter/absorption cytograms have distinct regions for platelets, red blood cells/reticulocytes/red cell coincidences, and white cells. The reticulocytes are distinguished from the mature red cells by statistical analysis of the red cell/reticulocyte absorption channel histogram. In the gated scatter/scatter cytogram, the eosinophil cell cluster is distinguished from the neutrophil cell cluster.

In general, the single channel method of the present invention involves the analysis of a larger number of blood cells in a blood sample to arrive at the differential cell information provided. For normal human blood samples, the ratio of red blood cells (RBCs) to white blood cells (WBCs) is about 500:1 to 1000:1. Thus, for example, in order to count approximately 1,000 WBCs to provide an adequate WBC count and WBC differential precision, about 500,000–1,000,000 RBCs generally have to be counted. However, this is not limiting for the present method in an automated system, since the analysis of 500,000 cells can be performed in a short time period, i.e., on the order of about 45 seconds, and certainly in less than about two minutes. In addition, adequate WBC count and WBC differential precision are simply achieved by repeated sampling from an aliquot containing as little as 1 microliter ($\mu l$) of whole blood suspended in the autoretic reagent. One microliter of normal human whole blood contains on the order of about 4,000,000–5,000,000 RBCs, 150,000–400,000 PLTs and 5,000–10,000 WBCs. As mentioned previously, the total analysis time including reaction time and counting is less than about two minutes.

Moreover, counting about 500,000–1,000,000 RBCs in the single channel method is particularly beneficial in the analysis of abnormal blood samples, for example, thrombocytopenic or highly thrombocytopenic blood samples, which have counts below about 20,000/microliter. In such samples, a single aspiration typically counts about 50,000 RBCs and about 200 or fewer PLTs, while about 2,000–4,000 PLTs are counted along with about 500,000 or 1,000,000 RBCs in accordance with the present method, thus improving PLT-counting precision. Therefore, the present method and system maintain efficiency and accuracy of blood sample analysis and do not significantly increase the time need to analyze a given blood sample.

Another advantage of the present invention is the elimination of the need for a large number of reagents depending on the cell types to be determined in a given channel of the analyzer. While one cell diluent reagent composition is used in the present single channel, single dilution method to form a reaction mixture or reaction solution with a blood sample aliquot, at least nine reagents were previously required for the analysis of the various blood cell types when using different channels of a hematology analyzer. In addition, as described, the present method is directly applicable to the analysis of normal blood samples and abnormal blood samples resulting from blood cell disorders, such as thrombocytopenia and hemolytic anemias.

One reason that current automated analyzers require multiple channels to count red blood cell types, platelet types and white blood cell types relates to the relative number of and counting frequency of red blood cells in these analyzers. In the vast majority of cases, red blood cells constitute more than 90 percent of all blood particles in a blood sample. As a result of the need to count adequate numbers of red cells in a practicably short amount of time, the counting frequency generates significant numbers of coincident events in the flow cell. Coincidence corresponds to the detection of more than one particle in the flow cell at any given time. The number of these events and their distribution in signal space typically obscures signals from certain white blood cell types (see Example 1).

Moreover, even if 50,000 red blood cells (e.g., a typical number) are counted in one analysis cycle, the number of white blood cells is typically under 100. This is too small a number to provide accurate and reproducible white blood cell counts or differentials on automated analyzers. As a result, red blood cells and platelets are enumerated in one measurement cycle (and white blood cells are also encountered), and white blood cells are enumerated in at least one other cycle that includes lysis of red blood cells and requires a much lower dilution factor than that for red blood cell/platelet analysis in order to encounter adequate numbers of white blood cells; typically 5,000–10,000. The present invention overcomes the difficulty associated with obscuring white blood cells by red blood cell coincidence signals by adding a third measurement dimension (light absorption or fluorescence) which serves to distinguish white blood cells from coincidences. Having overcome the difficulty associated with coincidence, the invention affords the benefit of even higher counting frequencies; as high as 4 times the typical rate. This much higher rate, coupled with extended counting time, permits the analysis of suitable numbers of white blood cells for providing accurate counts and differentials, i.e., on the order of 500–1,000 or more.

A general description of the single channel, single dilution method of the present invention follows. The reagent composition is mixed with an aliquot of a whole blood sample. For example, a 2-microliter aliquot of the whole blood sample is aspirated and then suspended in 1.25 milliliters of autoretic reagent (e.g., ADVIA® 120 Autoretic Reagent). The mixture is allowed to react at room temperature for about 10–15 (preferably about 13) seconds, during which time red blood cells, including reticulocytes, are sphered, and the reticulocytes, including reticulated platelets, and white blood cells are stained. The mixture is then passed essentially one cell at a time through an optical flow cell in a single channel of an automated hematology analyzer. The operating principles of automated hematology analyzer systems associated with the practice of the present method, for example, the Bayer H*™ Systems and ADVIA® System analyzers, are described in U.S. Pat. No. 5,817,519 to D. Zelmanovic et al. and in U.S. Pat. No. 6,114,173 of D. Zelmanovic et al., the contents of which are incorporated herein by reference. The general features of such analyzer systems are set forth below.

In the present, automated, single channel method, blood cells are analyzed together in the analyzer's single optical measurement channel, which includes a laser light source, a flowcell, two optical scattering detectors and one absorption or fluorescence detector. By means of hydrodynamic focusing, single cells are passed through the sensing zone of the flow cytometer, where they are illuminated by a focused light source having a suitable illumination wavelength. At least one, preferably two, scattering light signals, and at least either one absorption signal, or one fluorescence signal, are measured for the cells on a cell-by-cell basis by a detection system which measures scattered and either absorption or fluoresced light. From these measurements and related cytogram analysis, blood cells in the sample are identified, differentiated, and various parameters determined, using the technique(s) of scatter/scatter and scatter/scatter/absorption or scatter/scatter/fluorescence flow cytometry.

A fully automated apparatus for performing blood sample analyses using the single channel method of the present invention generally comprises a blood and reagent metering devices to provide the proper volume of each of the reaction components and a means for adequately mixing the components together, a reaction chamber, and a means for transferring the mixture to the measurement device. The measurement device comprises a means for providing a metered flow of the cell-containing reaction mixture through a flow cell for cell counting and enumeration. In general, light from the Helium-Neon laser or laser diode is incident upon the flow cell and this light is interrupted by the passage of blood cells through the flow cell. The blood cells scatter light as they intercept it, and, in the case of the stained nucleic acid of reticulocytes and white blood cells, absorb light as well.

A device or apparatus in accordance with the single channel method and system of present invention would be compact in size, as it needs to contain only a single reaction chamber and a single optical channel or measurement channel comprising the flow cell detectors which handle the optical and absorption or fluorescence signals derived from the cells as they pass through the flow cell. It is to be understood that such a device or apparatus would contain all of the hardware and software components necessary to carry out and perform the blood sample analyses as described herein, for example, a sample delivery pump, a sheath delivery pump, an aspirating mechanism or aspirator for uptake of a blood sample admixed with the blood diluent reagent and delivery to the automated system, a rinsing mechanism, and associated components, a results storage component, e.g., a computer, or computerized device, for storing results, and a printing and/or display component, e.g., to visualize cytograms.

More specifically, but not intended to be limiting for the present method, the measurement device used to carry out the single channel method includes three optical detectors. Two of the detectors detect light scattered at about 1°–5° and about 4°–25°, respectively, preferably at about 2°–3° and 5°–15°, respectively, from the axis of incidence. The third detector determines either the fraction of light absorbed or the fluorescence intensity. The signals from the three detectors are analyzed by a computer, which uses Mie Scattering Theory-derived tables to convert the signals into cell volume, component concentration and mass content data for each cell which passes through the flow cell. The computer also displays cytograms of the various scatter versus scatter, scatter versus absorption, or scatter versus fluorescence plots for the cell suspension, and uses mathematical algorithms to distinguish and differentiate among red blood cells, reticulocytes, white blood cells, platelets, reticulated platelets and coincidence signals.

A schematic depiction of the optical detection system employed in the single channel method according to the present invention is shown in FIG. 10. In this schematic, the low and high scatter signals are shown as $S_L$ and $S_H$, respectively. For $S_L$, the first stage signal amplification depicted is that of low angle, low gain. For $S_H$, the first stage signal amplification depicted is that of high angle, low gain. For $S_L$, the second stage signal amplification depicted is that of low, angle, high gain, while for $S_H$, the second stage signal amplification depicted is that of high angle, high gain. The absorption signal is also shown (Abs). The absorption signal (Abs) could be replaced with the fluorescence signal (FL), if fluorescence were being detected in accordance with an aspect of the present invention.

A detailed description of the practice of the single channel, single dilution method according to the present invention is as follows: One to two microliters of whole blood, anticoagulated with $K_3EDTA$, are aspirated and then drawn into a reaction chamber where the blood is mixed with autoretic reagent in the ratio of 625 volumes of reagent to 1 volume of blood to form a reaction mixture comprising the blood cell sample and the reagent composition. The reagent composition effectively isovolumetrically spheres the red blood cells and white blood cells. The platelets are effectively sphered by the $K_3EDTA$ anticoagulant.

The mixture is allowed to react for about 13 seconds and then a total of about 125 microliters of this mixture is pumped through an optical flow cell in 5 successive 25 microliter aliquots, or another microliter combination, so that a total of 0.2 microliters of whole blood is analyzed. For normal mammalian blood samples, this volume contains about 800,000 or more red blood cells, about 20,000 or more platelets and about 1,000 or more white blood cells.

The process of drawing each 25 microliter aliquot from the reaction chamber and pumping it through the optical flow cell takes about 15 seconds or less. The total cycle time is therefore about 88 seconds or less. As the mixture is pumped through the flow cell, it is sheathed by the sheath/rinse reagent. The sheathing narrows the mixture flow stream so that the blood cells pass through the flow cell essentially one at a time, and at a rate that permits their recognition by the optical detectors as well as their analysis by the computing software.

As each cell passes through the flow cell, it interrupts a focused beam of light, resulting in the, scattering and partial absorption or fluorescence of the incident beam. The scattering by the spherical cells, for a given wavelength of incident radiation, is a function of cell size and refractive index. Two detectors are in place to collect the light scattered within low and high angle ranges of preferably from approximately 1–10 degrees, preferably from approximately 1–7 degrees, more preferably from approximately 2–5 degrees, and most preferably from approximately 2–3 degrees for the low angle; and from approximately 4–30 degrees, preferably approximately 5–25 degrees, and more preferably, approximately 5–15 degrees for the high angle range. Thus, for each cell analyzed in the flow cell, a high scatter ($S_H$) and a low scatter ($S_L$) signal is detected. A detector is also in place to determine the fraction of light absorbed by each cell, or, alternatively, to determine the fluorescence intensity.

Each scattering signal undergoes either one or two stages of signal amplification. Such signal amplification is described in U.S. Pat. No. 5,817,519 to D. Zelmanovic et al. Briefly, as described for platelets, if the optical signals arise from approximately 2–3 degree scattering, platelets are amplified about 20- to 35-fold over the corresponding red blood cell signals, preferably about 30-fold. If the optical signals arise from 5°–15° scattering or from 8.5°–25° scattering, they are amplified about 8- to 15-fold, preferably about 12-fold.

The first stage of amplification, as applied specifically for red cells or white cells, i.e., low gain signal amplification, renders the signals suitable for the detailed analysis of red blood cells (including reticulocytes) and white blood cells. That is, the first stage amplification signal analysis includes the discrimination of red blood cells from other cell types, as well as the discrimination of neutrophils, lymphocytes+ basophils, monocytes and eosinophils from other blood cell types. This is partially visualized on an ungated low gain scatter/scatter cytogram (See, for example, FIG. 1C).

For analysis, the different cell types are mutually distinguishable by reference to their parameter value ranges, as provided in Tables 2 and 3. Different combinations of values in the tables give unique positions for each of the cell types in an analyzed blood sample in scatter/scatter/-absorption or fluorescence space.

The second stage of amplification, involving high gain amplification signals, renders the platelet signals suitable for detailed analysis by providing information for enumerating and determining the qualitative parameters for platelets, including discrimination from the other cell types, as depicted in Table 4, and the determination of cell volume and refractive index values. Visualization of the platelet signals from the second stage of signal amplification occurs via a high gain scatter/scatter cytogram. For platelets, as for red blood cells and white blood cells, the refractive index information is expressed in terms of the linearly-related parameter of platelet component concentration (MPC).

In another embodiment of the present invention, WBC can be distinguished from RBC on the basis of refractive index (r.i.), which is linearly related to cell density, by determining the ratio of the wavelength of incident light, i.e., absorbance (Abs, nanometers (nm)), versus the r.i. (or density), e.g., Abs/r.i, values of the cells. The wavelength of incident light at which absorption occurs is narrow banded from between 625 nm to 690 nm, preferably, between 630 nm to 675 nm, and more preferably, between 633 nm to 670 nm. In general, WBC have lower r.i. and a higher absorbance value as a consequence of their nucleic acid component. Thus, the determination of the Abs/r.i. ratio allows the separation of WBC from RBC.

For the scatter/scatter/fluorescence aspect of the present invention, the absorption detector is replaced with a fluorescence detector, which may be a photodiode or a photomultiplier tube. A portion of one of the scattering signals may be diverted in the direction of the fluorescence detector by placing an optical beam splitter, such as a dichroic mirror, in the path from the flow cell to one of the scattering detectors, for example, the 5–15 degree scattering detector. A wavelength filter, which effectively passes only light of longer wavelengths than the incident beam, is interposed between the beam splitter and the fluorescence detector in order to filter out the non-fluorescent component.

As mentioned earlier herein, several advantages are afforded by the practice of the present method and system. One is that, compared with prior methods, significantly fewer numbers of reagents are necessary in order to complete a blood sample analysis and identify and distinguish various blood cell types by employing one channel of an analyzer (i.e., wherein two reagents are used) compared with multiple or many discrete channels, each requiring a different reagent, such that five to nine different reagents are used.

The two principle reagents employed in the present single channel method are also more benign reagents for use analyzing red blood cell and white blood cell components of a whole blood sample. Not required by the present method of white cell analysis are reagent compositions that contain harsh surfactant and/or other ingredients to eliminate the red blood cells, for example. In spite of efforts by those in the art to design reagents that lyse red blood cells while not affecting other cell types in the sample, occasional lysis of the white blood cells and other unwanted effects may still occur, thereby leading to under-counting the white cells to be analyzed.

Additional advantages of the present method and system are that only one reaction chamber and measurement channel are required to obtain the results; only one or two microliters of a whole blood sample are required to obtain results; and only a single aliquot of a whole blood sample is required, thereby eliminating complex and expensive blood-aliquot apportioning hardware required of systems with multiple analysis channels.

Another embodiment of the present invention involves the analysis of blood samples from non-human mammalian species, i.e., a multispecies analysis method, useful, for example, for the analysis of feline (e.g., cat) blood. It has been newly determined that the peroxidase channel of an automated hematology analyzer, such as the Bayer ADVIA® 120 Analyzer, is not suitable for resolving eosinophils from neutrophils when a cat blood sample is analyzed. This is due to the lack of peroxidase staining of the eosinophils and the inability to distinguish the slightly- or lightly-stained eosinophils from the neutrophils. However, in the single channel method according to the present invention, scatter/scatter and absorption or fluorescence signals are used to distinguish the white blood cells, particularly the eosinophils, in a cat blood sample from all of the other cells. By this method, the eosinophils occupy unique region in the gated scatter/scatter cytogram plot from the other white blood cell types (see Example 3), so that both identification and quantification data can be obtained.

In sum, the present invention provides a single channel method for discriminating, identifying and measuring red blood cells, including reticulocytes, white blood cells, platelets and reticulated platelets in a mammalian blood sample, and for determining qualitative and quantitative parameters of the blood sample components by employing scattering and absorption or fluorescence signals, signal amplification and cytogram depictions following flow cytometric analysis, including Mie Scattering Theory. The present invention also embraces a more streamlined, compact and space-saving hematology analyzer apparatus for performing the single channel method as described. For example, as detailed above, the apparatus would require only one reaction chamber and one measurement channel to obtain the CBC/Diff/Retic results afforded by the method.

In its broad aspect, the method of the present invention comprises mixing an aliquot of the blood sample with an aqueous reagent composition to form a reaction mixture, where the reagent composition comprises an organic dye compound, preferably a cationic dye compound, in an amount effective to stain reticulocyte RNA and white blood cell nucleic acid, a surfactant as sphering agent in an amount effective to substantially isovolumetrically sphere red blood cells, reticulocytes, and white blood cells, and a buffer or buffer solution or buffer mixture, which maintains a neutral or near-neutral pH of the reagent composition. Optimally, the dye compound does not precipitate out of the reaction mixture formed between an aliquot of the blood sample and the reagent composition.

The reaction mixture containing the blood cells and reagent composition is passed substantially one cell at a time through a flow cell. Each cell within the flow cell interrupts a focused light source wherein the light is scattered and absorbed (or fluoresced). The scattered light is detected at a particular pair of angel intervals for amplifying the scattering signal, with the two intervals being an approximately 1 to 10 degree low angle interval, preferably a 1 to 7 degree low angle interval, more preferably, a 2 to 5 degree low angle interval, and most preferably, a 2 to 3 low angle interval; and an approximately 4 to 30 degree high angle interval, preferably, a 5 to 25 high angle interval, and more preferably, a 5 to 15 high angle interval, by two optical detectors to produce two scattering intensity measurements, a high scatter and a low scatter.

Each scattering signal undergoes two sets of stages of amplification, with the first set of stages rendering the signals of red blood cells, reticulocytes and white blood cells suitable for analysis, and the second stage rendering the signals of platelets suitable for analysis. A detector is also in place for detecting either absorption or fluorescence of incident radiation resulting from binding of the dye compound to reticulocyte and white blood cell nucleic acid, or components thereof. The method allows the discrimination among and measurement of different blood cell and platelet components of the sample by determining scatter/scatter/-absorption or -fluorescence spatial parameters using the scattering and absorption or fluorescence signals detected by the system's optical detectors.

EXAMPLES

The examples as set forth herein are meant to exemplify the various aspects of carrying out the invention and are not intended to limit the invention in any way.

Example 1

In Example 1, the utility and success of the above-described single channel method in the analysis of a normal human whole blood sample was demonstrated. A $K_3$EDTA-anticoagulated human whole blood sample was analyzed according to the method of the invention using the autoretic and sheath/rinse reagent compositions and including absorption gating in the presentation of the cytogram display results shown in FIGS. 2A–2C.

The reaction mixture of blood cells and autoretic reagent was aspirated 10 times and approximately 50,000 cells were counted each time. Specifically, one to two microliters of the anticoagulated human whole blood sample were aspirated and then drawn into a reaction chamber. In the reaction chamber, the blood aliquot was mixed with ADVIA® 120 Autoreticulocyte reagent in the ratio of 625 volumes of reagent to 1 volume of blood to form a reaction mixture. The ADVIA® 120 Sheath/Rinse was also used.

The blood/reagent mixture was allowed to react for about 13 seconds and then a total of 7 microliters was pumped through an optical flow cell in 5 successive 7 microliter aliquots.

The results of this experiment are presented in FIGS. 1A–1C and 2A–2C. In FIGS. 1A–1C, the control Peroxidase Channel cytogram (FIG. 1A), as well as the ungated versions of the scatter/absorption cytogram (FIG. 1B) and the scatter/scatter cytogram (FIG. 1C) are displayed. In FIGS. 2A–2C, the control Peroxidase Channel cytogram (FIG. 2A), along with the gated versions of the scatter/absorption cytogram (FIG. 2B) and the scatter/scatter cytogram (FIG. 2C) are shown. A comparison of the ungated and gated scatter/scatter cytograms shows that the neutrophils and eosinophils are not separable from red cell coincidences in scatter/scatter space but are distinct in scatter/scatter/absorption space. Comparison of the relative numbers of white cell types in the ungated (FIG. 1C) and gated (FIG. 2C) scatter/scatter cytograms with those in the Peroxidase Channel cytogram shows qualitative agreement.

In this example and those that follow, the scattering detectors collected light scattered from 2°–3° and from 5°–15°. The absorption detector collected light transmitted in the forward direction.

The WBC Differential displays presented in FIGS. 1A–1C and 2A–2C and in the following figures contain numerical data at low (L) and/or high (H) gain for WBC (white blood cell count), Neut (neutrophils), Lymph (lymphocytes); Mono (monocytes), Eos (eosinophils), Baso (basophils), LUC (large unstained lymphocytes), LI (lobularity index) and MPXI (mean peroxidase activity index, which is associated with the position and angle of the neutrophil ball).

Example 2

The experiment presented in Example 2 was performed to demonstrate the discrimination of white blood cells in the absence of coincidences. In this example, platelet rich plasma (PRP) was analyzed according to the method of the invention, using the autoretic reagent (ADVIA® 120 Autoreticulocyte Reagent and the sheath/rinse reagent (ADVIA® 120 Sheath/Rinse). A $K_3$EDTA-anticoagulated human whole blood sample was centrifuged to remove virtually all of the red blood cells, leaving platelets, white blood cells and only a few red blood cells in a plasma suspension. No absorption gating was necessary for the corresponding cytogram displays, since coincidence signals were absent. The sample was aspirated 10 times and the method of sample analysis was as described above for Example 1.

Figure 3A:
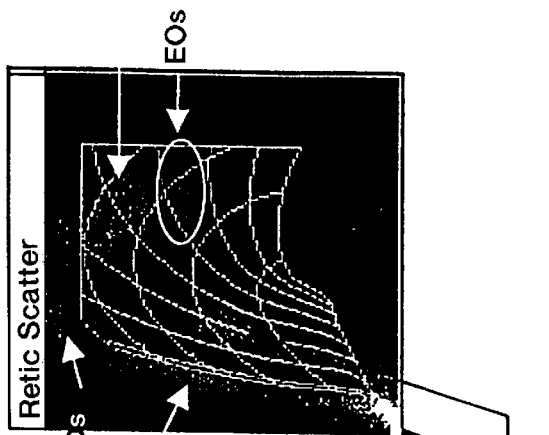
FIGS. 3A–3C show cytograms for the sum of ten aspirations of platelet-rich plasma (PRP). The FIGS. 3A–3C cytograms are shown to demonstrate the expected positions of the various WBC types on the scatter/scatter cytograms, in the absence of coincidence. These are seen to be the positions occupied by the same WBC types as those on cytograms produced by the single channel method (or on the reticulocyte channel cytograms). In general. coincidence signals are due to the presence of two or more cells (typically red cells, which comprise approximately 95% of all blood cells in normal mammalian blood samples) in the optical detection chamber at the same time. The coincidence signals are larger than the signals due to individual cells, and they occupy the same scatter/scatter space as the PMN white blood cells. However, neutrophils and eosinophils absorb significantly more light than do red blood cells (and their coincidences), platelets, and even reticulocytes. On this basis, white cells may be "gated" (i.e., a technical means of isolating the cells in two- or three-dimensional space as visualized on a cytogram) from other cell types and subsequently analyzed in scatter/scatter space. The purpose of this is to distinguish among neutrophils, eosinophils, and basophils based on their positions in scatter/scatter space.
Figure 3B:
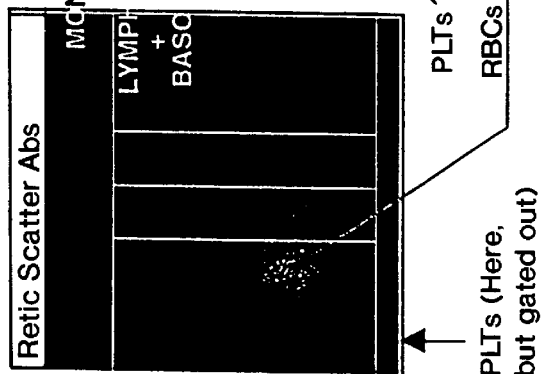
Figure 3C:
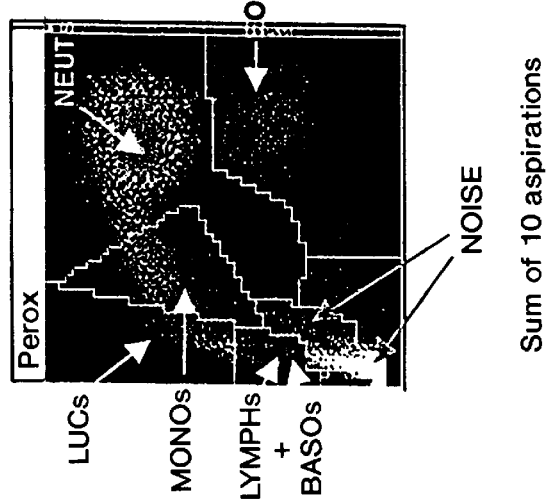

The results of this experiment are shown in FIGS. 3A–3C. The reticulocyte channel scatter/absorption cytogram (FIG. 3B) and scatter/scatter cytogram (FIG. 3C) for the sum of 10 aspirations of approximately 5,800 cells each (enriched in platelets and white cells) were displayed, along with the Peroxidase Channel cytogram (FIG. 3A), as a reference control. Numerical WBC differential results are also shown.

The experiment presented in Example 2 was performed to demonstrate the expected positions for the various white blood cell types on the scatter/scatter cytogram (ungated low gain cytogram) in the absence of red blood cell coincidences that obscure neutrophils and eosinophils. The relative numbers of white cell types appearing in the scatter/scatter cytogram qualitatively agree with the relative numbers in the reference Peroxidase Channel cytogram control. It is to be understood that the lymphocytes enumerated by the method of the invention include both the lymphocytes and LUCs (large unstained cells) which are enumerated by the Peroxidase channel.

Example 3

In this example, the multispecies aspect of the single channel method was demonstrated in the analysis of a mammalian whole blood sample other than a human whole blood sample. Accordingly, four different feline whole blood samples were analyzed by the single channel method of the present invention employing the method as described in Example 1 for the human blood sample. The results of the analyses of three of the four different cat blood samples are presented in FIGS. 4A–4C through 9A–9C.

Each sample was aspirated once and approximately 150,000 feline cells were counted each time. The results of three separate experiments are presented in FIGS. 4A–4C through 9A–9C. All of the figures include reference peroxidase channel cytograms, as well as ungated scatter/absorption cytograms and scatter/scatter cytograms and their gated counterparts. It is to be noted that, in contrast to the human blood sample Peroxidase cytograms, (FIGS. 1A and 2A, for example), feline Peroxidase cytograms (FIGS. 4A and 7A; 5A and 8A; 6A and 9A) do not display distinct eosinophil clusters. This is due to the peroxidase negativity of feline eosinophils. However, the gated scatter/scatter cytograms show distinct eosinophil clusters for eosinophil percentages of 2% to 16% in the three samples represented.

In particular, FIGS. 4A–4C, 5A–5C and 6A–6C depict the cytograms showing the ungated results from the three experiments analyzing cat whole blood cells. FIGS. 7A–7C, 8A–8C and 9A–9C depict the cytograms showing the gated results that correspond with the ungated cytogram results shown in FIGS. 4A–4C, 5A–5C and 6A–6C, respectively.

The ungated scatter/scatter cytograms (FIGS. 4C, 5C, and 6C) include distinct clusters for red cells (including coincidences), platelets, lymphocytes (and monocytes), and some of the polymorphonuclear cells. The ungated scatter/ absorption cytograms (FIGS. 4B, 5B and 6B) have distinct clusters for platelets, red cells/reticulocytes/red coincidences, and white cells. The reticulocytes were distinguished from the mature red cells by statistical analysis of the red cell/reticulocyte absorption channel histogram.

The gated scatter/scatter cytograms (FIGS. 7A–7C, 8A–8C and 9A–9C) include cells whose absorption signals appear in the saturation absorption channel (channel 99 of the absorption axis of the scatter/absorption cytogram, where the absorption axis ranges from channel 0 to channel 99).

As noted above, in the gated scatter/scatter cytograms (FIGS. 7C, 8C and 9C), the eosinophil cluster is distinguished from the neutrophil cluster. That the present method allows for the distinction of eosinophils from neutrophils in the feline sample analysis, while methods involving the peroxidase channel do not, is another benefit of the method and reagents of the present invention.

A further benefit of the present single channel method and system is apparent from a comparison of the reference Peroxidase cytograms and the ungated and gated scatter/ scatter cytograms in the examples and figures presented herein. All of the Peroxidase cytograms have a "noise" region in close proximity of the lymphocyte region, consisting of platelets and some red blood cell stroma. Algorithms are required for distinguishing non-lymphocyte noise from lymphocytes. On occasion, these regions may become confused, leading to potential error in the lymphocyte count as well as the overall white cell count. In contrast, in the practice of the present method, no such noise region appears in proximity of the lymphocytes, thereby eliminating this potential source of error in lymphocyte counts.

Example 4

In this example, reticulated platelets were analyzed by the present invention. A whole blood sample was diluted 625-fold in Bayer Autoretic reagent and approximately 50,000 cells were analyzed in a hematology analyzer using the single channel, single dilution method as described herein. The reticulated platelets were distinguished from mature platelets by their greater absorption of light due to uptake of nucleic acid specific dye. The results are presented in FIGS. 1A–1E.

The contents of all patent applications, issued patents, published articles and references, and textbooks as cited herein are hereby incorporated by reference in their entirety to more fully describe the state of the art to which the present invention pertains.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

What is claimed is:

1. A single channel, single dilution method for identifying and measuring cell components in a normal or abnormal mammalian blood sample, comprising mature red blood cells; reticulocytes; white blood cells, including lymphocytes, basophils, eosinophils, monocytes, and neutrophils; platelets and reticulated platelets, and for determining qualitative and quantitative parameters of said blood sample components, comprising:

(a) mixing in a single dilution an aliquot of the blood sample with an aqueous reagent composition to form a reaction mixture, said reagent composition comprising a surfactant as sphering agent in an amount effective to sphere blood cells in the sample; a dye compound in an amount effective to stain reticulocyte RNA and white blood cell nucleic acid; and a buffer or buffer solution; wherein the red blood cells remain substantially unlysed in the reaction mixture;

(b) passing the reaction mixture of (a) substantially one cell at a time through a flow cell in a single channel, wherein light is scattered and absorbed by each cell component; said scattered light being optically detected at a low angle interval of about 1 to 10 degrees to produce a low light scatter intensity measurement and at a high angle interval of about 4 to 30 degrees to produce a high light scatter intensity measurement;

(c) detecting absorption signals produced by incident radiation resulting from binding of the dye compound to reticulocyte and white blood cell nucleic acid, or components thereof, in the single channel; and (d) discriminating among and measuring each of the different blood cell components, comprising mature red blood cells; reticulocytes; white blood cells, including lymphocytes, basophils, eosinophils, monocyte, and neutrophils; platelets and reticulated platelets of the sample by detecting scatter-scatter optical signals, scatter-absorption optical signals, or scatter-scatter-absorption optical signals by means of the scattering measurements and absorption signals of steps (b) and (c); wherein detection and measurement are performed on each of the cell components flowing through the flow cell in the single channel.

2. The method according to claim 1, wherein, in (b), said low and high scatter intensity measurements undergo a first and second amplification; wherein said first amplification renders signals of the mature red blood cells; reticulocytes; and the white blood cells, including lymphocytes, basophils, eosinophils, monocytes, and neutrophils, suitable for analysis, and said second amplification renders signals of the platelets and reticulated platelets suitable for analysis.

3. The method according to claim 1, wherein the low angle interval of step (b) is about 1–7 degrees and the high angle interval is about 5–25 degrees.

4. The method according to claim 1, wherein the low angle interval of step (b) is about 1–5 degrees and the high angle interval is about 5–15 degrees.

5. The method according to claim 1, wherein the low angle interval of step (b) is about 2–3 degrees and the high angle interval is about 5–15 degrees.

6. The method according to claim 1, wherein in said discriminating step (d), (i) platelets and reticulated platelets are resolved from other blood cells based on scatter-scatter parameters; (ii) red blood cells are resolved from platelets based on scatter-scatter parameters; (iii) red blood cells are resolved from reticulocytes based on scatter-absorption parameters; (iv) red blood cells are resolved from lymphocytes, basophils and monocytes based on scatter-scatter parameters; (v) red blood cells are resolved from neutrophils and eosinophils based on scatter-scatter-absorption parameters; (vi) lymphocytes and basophils are resolved from monocytes based on scatter-scatter-absorption parameters; and (vii) neutrophils are resolved from eosinophils based on scatter-scatter parameters plus gating of red blood cell and reticulocyte signals based on absorption parameters.

7. The method according to claim 1, wherein the buffer or buffer solution of step (a) maintains a reagent composition pH of about 6 to about 9.

8. The method according to claim 1, wherein the buffer or buffer solution of step (a) maintains a reagent composition pH of about 7.2 to about 7.5.

9. The method according to claim 8, wherein the buffer or buffer solution of step (a) maintains a reagent composition pH of about 7.4.

10. The method according to claim 1, wherein the buffer or buffer solution is isotonic, thereby providing substantially isovolumetric sphering of the blood cells.

11. The method according to claim 1, wherein the blood sample aliquot of (a) comprises about 1–2 microliters.

12. The method according to claim 1, wherein the dye compound in the reagent composition of step (a) is a cationic dye compound.

13. The method according to claim 12, wherein the cationic dye compound is Oxazine 750.

14. The method according to claim 13, wherein Oxazine 750 is present in the reagent composition in an amount of about 2 µg/ml to about 15 µg/ml.

15. The method according to claim 13, wherein Oxazine 750 is present in the reagent composition in an amount of about 6 µg/ml to about 20 µg/ml.

16. The method according to claim 13, wherein Oxazine 750 is present in the reagent composition in an amount of about 9 µg/ml to about 10.5 µg/ml.

17. The method according to claim 12, wherein the cationic dye compound in the reagent composition of step (a) is New Methylene Blue.

18. The method according to claim 17, wherein New Methylene Blue is present in the reagent composition in an amount of from about 10 µg/ml to about 100 µg/ml.

19. The method according to claim 1, wherein the surfactant in the reagent composition of (a) is selected from the group consisting of nonionic surfactants and zwitterionic surfactants.

20. The method according to claim 19, wherein the surfactant is a nonionic surfactant.

21. The method according to claim 20, wherein the nonionic surfactant is an alkylglycoside.

22. The method according to claim 21, wherein the nonionic surfactant is selected from the group consisting of n-dodecyl-β-D-maltoside, n-tetradecyl-β-D-maltoside and n-tetradecyl-β-D-glucoside.

23. The method according to claim 19, wherein the surfactant in the reagent composition of (a) is a zwitterionic surfactant.

24. The method according to claim 23, wherein the zwitterionic surfactant in the reagent composition of step (a) is an alkyl amido betaine or an alkyl betaine.

25. The method according to claim 23, wherein the zwitterionic surfactant is selected from the group consisting of lauramidopropyl betaine (LAB), cocoamidopropylbetaine (CAPB) and cocoamidosulfobetaine (CASB).

26. The method according to claim 25, wherein lauramidopropyl betaine (LAB) is present in the reagent composition in an amount of from about 12 µg/ml to about 87.5 µg/ml; cocoamidopropylbetaine (CAPB) is present in the reagent composition in an amount of from about 8.8 µg/ml to about 17.5 µg/ml; and cocoamidosulfobetaine (CASB) is present in the reagent composition in an amount of from about 12.5 µg/ml to about 15 µg/ml.

27. The method according to claim 1, wherein the surfactant in the reagent composition of step (a) is N-tetradecyl-N,N-dimethyl-3-ammonio-1-propanesulfonate (TDAPS) or N-dodecyl-N,N-dimethyl-3-ammonio-1-propanesulfonate (DDAPS).

28. The method according to claim 27, wherein N-tetradecyl-N,N-dimethyl-3-ammonio-1-propanesulfonate (TDAPS) is present in the reagent composition in an amount of from about 3.9 µg/ml to about 11.8 µg/ml and N-dodecyl-N,N-dimethyl-3-ammonio-1-propanesulfonate (DDAPS) is present in the reagent composition in an amount of from about 49.3 µg/ml to about 148 µg/ml.

29. The method according to claim 1, wherein the reagent composition of step (a) further comprises an alkali metal salt.

30. The method according to claim 29, wherein said alkali metal salt in the reagent composition of step (a) is sodium chloride or potassium chloride.

31. The method according to claim 1, wherein the reagent composition of step (a) further comprises an antimicrobial compound.

32. The method according to claim 31, wherein the antimicrobial compound in the reagent composition of step (a) is selected from the group consisting of one or more of 2-methyl-4-isothiazolin-3-one; 5-chloro-2-methyl-4-isothiazolin-3-one; N,N'-methylenebis[N'-(1-(hydroxymethyl)-2,5-dioxo4-imidazolidinyl]urea); (1-(3-chloroallyl)-3,5,7-triaza-1-azoniaadamantane chloride); and Bronopol 2-bromo-2-nitropropane-1,3-diol ($C_3H_6BrNO_4$).

33. The method according to claim 1, wherein said absorbed incident radiation of step (c) has an excitation wavelength in the red region of the spectrum.

34. The method according to claim 1, wherein said reagent composition of step (a) further comprises at least one nucleophile.

35. The method according to claim 34, wherein said nucleophile is an azide ($N_3^-$) or cyanate ($OCN^-$) ion.

36. The method according to claim 34, wherein said nucleophile is present in said reagent composition at a concentration of about 20 mM.

37. The method according to claim 1, wherein the osmolarity of the reagent composition of step (a) is about 250 to 300 milliosmoles.

38. The method according to claim 1, wherein the osmolarity of the reagent composition of step (a) is about 287 to 297 milliosmoles.

39. The method according to claim 1, wherein the blood sample being analyzed is a normal mammalian blood sample.

40. The method according to claim 1, wherein the qualitative and quantitative parameters are selected from the group consisting of red blood cell count, white blood cell count, platelet count, hemoglobin concentration, hematocrit, mean cell volume, mean cell hemoglobin, mean cell hemoglobin concentration, red blood cell volume distribution width, cellular hemoglobin concentration distribution width, mean platelet volume, mean platelet component concentration, mean platelet dry mass, percent and absolute count of neutrophils, percent and absolute counts of lymphocytes plus basophils, percent and absolute count of monocytes, percent and absolute count of eosinophils, percent and absolute count of reticulocytes, reticulocyte mean cell volume, reticulocyte mean cell hemoglobin, reticulocyte mean cell hemoglobin concentration, percent and absolute count of reticulated platelets, mean neutrophil volume, mean neutrophil component concentration, mean neutrophil dry mass, mean lymphocyte+basophil volume, mean lymphocyte+basophil component concentration, mean lymphocyte+basophil dry mass, mean monocyte volume, mean monocyte component concentration, mean monocyte dry mass, mean eosinophil volume, mean eosinophil component concentration and mean eosinophil dry mass.

41. The method according to claim 1, further comprising, following step (d), the step of rinsing the single channel to remove residual cell and reaction mixture accumulation, thereby preventing reagent buildup.

42. The method according to claim 1, wherein the blood sample is anticoagulated.

43. The method according to claim 42, wherein the blood sample is anticoagulated with $K_3$ EDTA.

44. The method according to claim 1, wherein cytograms display the regions occupied by the blood cells and platelets discriminated from each other in the method.

45. The method according to claim 44, wherein (i) red blood cells are distinguished from other blood cells in the sample based on regions occupied by the red blood cells in a low-gain, scatter-scatter space on the cytogram; (ii) lymphocytes plus basophils and monocytes are distinguished from other blood cells in the sample based on the regions occupied by the lymphocytes plus basophils and monocytes in a low-gain, scatter-scatter space on the cytogram; (iii) platelets and reticulated platelets are distinguished from other blood cells in the sample based on regions occupied by the platelets in a high-gain, scatter-scatter cytogram; (iv) reticulocytes are distinguished from other blood cells in the sample based on a statistical analysis of an absorption frequency histogram derived from positions occupied by mature red blood cells and reticulocytes in low-gain, high angle absorption space; and (v) neutrophils and eosinophils are distinguished from other blood cells in the sample based on regions occupied by the neutrophils and the eosinophils within scatter-scatter-absorption space.

46. The method according to claim 45, wherein neutrophils are further distinguished from eosinophils based on the regions that neutrophils and eosinophils occupy on a gated low-gain, scatter-scatter cytogram.

47. The method according to claim 1, wherein white blood cells are separated from red blood cells in step (d) on the basis of a ratio between wavelength of incident light and refractive index values of the blood cells.

48. The method according to claim 47, wherein the wavelength of incident light at which absorption occurs is narrow banded between 625 to 690 nanometers.

49. The method according to claim 1, wherein the blood sample being analyzed is an abnormal mammalian blood sample.

50. A single channel, single dilution method for discriminating and enumerating blood cell components comprising mature red blood cells; reticulocytes; white blood cells, including lymphocytes, basophils, eosinophils, monocytes, and neutrophils; platelets and reticulated platelets, and for determining qualitative and quantitative parameters in a mammalian blood sample, comprising:

(a) mixing in a single reaction chamber of a hematology analyzer, in a single dilution step, an aliquot of the blood sample with an aqueous reagent composition to form a reaction mixture, said reagent composition comprising a cationic dye compound in an amount effective to stain reticulocyte RNA and white blood cell nucleic acid, a surfactant in an amount effective to sphere blood cells in the sample, and a buffer or buffer solution; wherein the red blood cells remain substantially unlysed in the reaction mixture;

(b) passing the reaction mixture of step (a) substantially one cell at a time through a flow cell in the single chamber containing a single optical channel, wherein light is scattered and absorbed by each cell component; said scattered light being detected at a low angle interval of approximately 1 to 10 degrees and a high angle interval of approximately 4 to 30 degrees to produce low and high scatter intensity measurements, said low and high scatter intensity measurements undergoing a first and second amplification; wherein said first amplification renders signals of red blood cells including reticulocytes, and white blood cells, suitable for analysis and said second amplification renders signals of platelets suitable for analysis;

(c) detecting absorption signals produced by incident radiation resulting from binding of the dye compound to reticulocyte and white blood cell nucleic acid or components thereof in the single channel; and (d) discriminating among and measuring each of the different blood cell components, comprising mature red blood cells; reticulocytes; white blood cells, including lymphocytes, basophils, eosinophils, monocytes, and neutrophils; platelets and reticulated platelets of the sample by determining scatter-scatter spatial parameters, scatter-absorption spatial parameters, or scatter-scatter-absorption spatial parameters using said scattering measurements and absorption signals of steps (b) and (c); wherein detection and measurement are performed on each of the cell components flowing through the flow cell in the single channel of a cytometry analyzer.

51. The method according to claim 50, wherein the low angle interval of step (b) is about 1–7 degrees and the high angle interval is about 5–25 degrees.

52. The method according to claim 50, wherein in said discriminating step (d), (i) platelets and reticulated platelets are resolved from other blood cells based on scatter-scatter parameters; (ii) red blood cells are resolved from platelets based on scatter-scatter parameters; (iii) red blood cells are resolved from reticulocytes based on scatter-absorption parameters; (iv) red blood cells are resolved from lymphocytes, basophils and monocytes based on scatter-scatter parameters; (v) red blood cells are resolved from neutrophils and eosinophils based on scatter-scatter-absorption parameters; (vi) lymphocytes and basophils are resolved from monocytes based on scatter-scatter parameters; and (vii) neutrophils are resolved from eosinophils based on scatter-scatter parameters plus gating of red blood cell and reticulocyte signals based on absorption parameters.

53. The method according to claim 50, wherein the buffer or buffer solution of (a) maintains a reagent composition pH of about 6 to about 9.

54. The method according to claim 50, wherein the buffer or buffer solution of step (a) maintains a reagent composition pH of about 7.2 to about 7.5.

55. The method according to claim 50, wherein the buffer or buffer solution is isotonic, thereby providing substantially isovolumetric sphering of the blood cells.

56. The method according to claim 50, wherein the cationic dye compound in the reagent composition of step (a) is Oxazine 750.

57. The method according to claim 56, wherein Oxazine 750 is present in the reagent composition in an amount of about 2 µg/ml to about 15 µg/ml.

58. The method according to claim 50, wherein the cationic dye compound in the reagent composition of step (a) is New Methylene Blue.

59. The method according to claim 58, wherein New Methylene Blue is present in the reagent composition in an amount of from about 10 µg/ml to about 100 µg/ml.

60. The method according to claim 50, wherein the surfactant in the reagent composition of (a) is selected from the group consisting of nonionic surfactants and zwitterionic surfactants.

61. The method according to claim 60, wherein the surfactant is an alkylglycoside nonionic surfactant selected from the group consisting of n-dodecyl-β-D-maltoside, n-tetradecyl-β-D-maltoside and n-tetradecyl-β-D-glucoside.

62. The method according to claim 60, wherein the surfactant in the reagent composition of (a) is a zwitterionic surfactant.

63. The method according to claim 62, wherein the zwitterionic surfactant in the reagent composition of (a) is an alkyl amido betaine or an alkyl betaine.

64. The method according to claim 63, wherein the zwitterionic surfactant is selected from the group consisting of lauramidopropyl betaine (LAB), cocoamidopropylbetaine (CAPB) and cocoamidosulfobetaine (CASB).

65. The method according to claim 64, wherein lauramidopropyl betaine (LAB) is present in the reagent composition in an amount of from about 12 μg/ml to about 87.5 μg/ml; cocoamidopropylbetaine (CAPB) is present in the reagent composition in an amount of from about 8.8 μg/ml to about 17.5 μg/ml; and cocoamidosulfobetaine (CASB) is present in the reagent composition in an amount of from about 12.5 μg/ml to about 15 μg/ml.

66. The method according to claim 50, wherein the surfactant in the reagent composition of step (a) is N-tetradecyl-N,N-dimethyl-3-ammonio-1-propanesulfonate (TDAPS) or N-dodecyl-N,N-dimethyl-3-ammonio-1-propanesulfonate (DDAPS).

67. The method according to claim 66, wherein N-tetradecyl-N,N-dimethyl-3-ammonio-1-propanesulfonate (TDAPS) is present in the reagent composition in an amount of from about 3.9 μg/ml to about 11.8 μg/ml and N-dodecyl-N,N-dimethyl-3-ammonio-1-propanesulfonate (DDAPS) is present in the reagent composition in an amount of from about 49.3 μg/ml to about 148 μg/ml.

68. The method according to claim 50, wherein the reagent composition of step (a) further comprises an alkali metal salt.

69. The method according to claim 68, wherein said alkali metal salt in the reagent composition of step (a) is sodium chloride or potassium chloride.

70. The method according to claim 50, wherein the reagent composition of step (a) further comprises an antimicrobial compound selected from the group consisting of one or more of 2-methyl-4-isothiazolin-3-one; 5-chloro-2-methyl-4-isothiazolin-3-one; N,N'-methylenebis[N'-(1-(hydroxymethyl)-2,5-dioxo-4-imidazolidinyl]urea); (1-(3-chloroallyl)-3,5,7-triaza-1-azoniaadamantane chloride); and Bronopol 2-bromo-2-nitropropane-1,3-diol ($C_3H_6BrNO_4$).

71. The method according to claim 50, wherein said absorbed incident radiation of step (c) has an excitation wavelength in the red region of the spectrum.

72. The method according to claim 50, wherein said reagent composition of step (a) further comprises at least one nucleophile.

73. The method according to claim 72, wherein said nucleophile is an azide ($N_3^-$) or cyanate ($OCN^-$) ion.

74. The method according to claim 50, wherein the osmolarity of the reagent composition of step (a) is about 250 to 300 milliosmoles.

75. The method according to claim 50, wherein the osmolarity of the reagent composition of step (a) is about 287 to 297 milliosmoles.

76. The method according to claim 50, wherein the blood sample being analyzed is a normal or an abnormal mammalian blood sample.

77. The method according to claim 50, wherein the determined parameters are selected from the group consisting of red blood cell count, white blood cell count, platelet count, hemoglobin concentration, hematocrit, mean cell volume, mean cell hemoglobin, mean cell hemoglobin concentration, red blood cell volume distribution width, cellular hemoglobin concentration distribution width, mean platelet volume, mean platelet component concentration, mean platelet dry mass, percent and absolute count of neutrophils, percent and absolute counts of lymphocytes plus basophils, percent and absolute count of monocytes, percent and absolute count of eosinophils, percent and absolute count of reticulocytes, reticulocyte mean cell volume, reticulocyte mean cell hemoglobin, reticulocyte mean cell hemoglobin concentration, percent and absolute count of reticulated platelets, mean neutrophil volume, mean neutrophil component concentration, mean neutrophil dry mass, mean lymphocyte+basophil volume, mean lymphocyte+basophil component concentration, mean lymphocyte+basophil dry mass, mean monocyte volume, mean monocyte component concentration, mean monocyte dry mass, mean eosinophil volume, mean eosinophil component concentration and mean eosinophil dry mass.

78. The method according to claim 50, further comprising, following step (d), the step of rinsing the single channel to remove residual cell and reaction mixture accumulation, thereby preventing reagent buildup.

79. The method according to claim 50, wherein the blood sample is anticoagulated.

80. The method according to claim 79, wherein the blood sample is anticoagulated with $K_3$ EDTA.

81. The method according to claim 50, wherein cytograms display regions occupied by the mature red blood cells; reticulocytes; white blood cells, including lymphocytes, basophils, eosinophils, monocytes, and neutrophils; platelets; and reticulated platelets discriminated from each other in the method.

82. The method according to claim 81, wherein (i) red blood cells are distinguished from other blood cells in the sample based on regions occupied by the red blood cells in a low-gain, scatter-scatter space on the cytogram; (ii) lymphocytes plus basophils and monocytes are distinguished from other blood cells in the sample based on the regions occupied by the lymphocytes plus basophils and monocytes in a low-gain, scatter-scatter space on the cytogram; (iii) platelets and reticulated platelets are distinguished from other blood cells in the sample based on regions occupied by the platelets in a high-gain, scatter-scatter cytogram; (iv) reticulocytes are distinguished from other blood cells in the sample based on a statistical analysis of an absorption frequency histogram derived from positions occupied by mature red blood cells and reticulocytes in low-gain, high angle absorption space; and (v) neutrophils and eosinophils are distinguished from other blood cells in the sample based on regions occupied by the neutrophils and the eosinophils within scatter-scatter-absorption space.

83. The method according to claim 82, wherein eosinophils are discriminated from the other blood cell and platelet components of the sample by determining a region occupied by the eosinophils within scatter-scatter-absorption space.

84. The method according to claim 82, wherein neutrophils are further distinguished from eosinophils based on the regions occupied by the neutrophils and the eosinophils on an absorption-gated low-gain, scatter-scatter cytogram.

85. The method according to any of claims 82 to 84, wherein the eosinophils are in a non-human mammalian blood sample.

86. The method according to claim 85, wherein the blood sample is a feline blood sample.

87. The method according to claim 50, wherein the white blood cells are discriminated from the red blood cells in step (d) on the basis of a ratio between wavelength of incident light and refractive index values of the red and white blood cells.

88. The method according to claim 87, wherein the wavelength of incident light at which absorption occurs is narrow banded between 625 to 690 nanometers.

89. An apparatus for performing a single channel, single dilution method for identifying and measuring cell components comprising mature red blood cells; reticulocytes; white blood cells, including lymphocytes, basophils, eosinophils, monocytes, and neutrophils; platelets and reticulated platelets in a normal or abnormal mammalian blood sample, and for determining qualitative and quantitative parameters of said blood sample components, said apparatus comprising:

(a) an aspirator mechanism for providing an aliquot of the blood sample;

(b) a reaction chamber wherein (i) the aliquot of the blood sample is mixed in a single dilution step with an aqueous reagent composition to form a reaction mixture, said reagent composition comprising a dye compound in an amount effective to stain reticulocyte RNA and white blood cell nucleic acid, a surfactant as sphering agent in an amount effective to sphere blood cells and reticulocytes, and a buffer or buffer solution; wherein the red blood cells remain substantially unlysed in the reaction mixture; and (ii) the reaction mixture of (i) comprising the blood cells and platelets is passed substantially one cell at a time through a flow cell in a single optical channel by means of a suitable pump and within a suitable sheathing provided by the pump, wherein light is scattered and absorbed by each cell component; said scattered light being detected at a low angle interval of about 1 to 10 degrees to produce a low light scatter intensity measurement and at a high angle interval of about 4 to 30 degrees to produce a high light scatter intensity measurement;

(c) an optical detector for detecting absorption signals produced by incident radiation resulting from binding of the dye compound to reticulocyte and white blood cell nucleic acid or components thereof in the single channel; and (d) a computer for discriminating among and measuring each of the different blood cell components, comprising mature red blood cells; reticulocytes; white blood cells, including lymphocytes, basophils, eosinophils, monocytes, and neutrophils; platelets and reticulated platelets of the sample by determining scatter-scatter spatial parameters, scatter-absorption spatial parameters, or scatter-scatter-absorption spatial parameters by using, computing and displaying said scattering measurements and absorption signals of (b) and (c); wherein detection and measurement are performed on each of the cell components flowing through the flow cell in the single channel.

90. The apparatus according to claim 89, wherein, in (b)(ii), said low and high scatter intensity measurements undergo a first and second amplification; wherein said first amplification renders signals of the mature red blood cells; reticulocytes; and white blood cells, including lymphocytes, basophils, eosinophils, monocytes and neutrophils suitable for analysis, and said second amplification renders signals of the platelets and reticulated platelets suitable for analysis.

91. The apparatus according to claim 89, wherein the low angle interval of (b) is about 1–7 degrees and the high angle interval is about 5–25 degrees.

92. The apparatus according to claim 89, wherein in (d),(i) platelets and reticulated platelets are resolved from other blood cells based on scatter-scatter parameters; (ii) red blood cells are resolved from platelets based on scatter-scatter parameters; (iii) red blood cells are resolved from reticulocytes based on scatter-absorption parameters; (iv) red blood cells are resolved from lymphocytes, basophils and monocytes based on scatter-scatter parameters; (v) red blood cells are resolved from neutrophils and eosinophils based on scatter-scatter-absorption parameters; (vi) lymphocytes and basophils are resolved from monocytes based on scatter-scatter parameters; and (vii) neutrophils are resolved from eosinophils based on scatter-scatter parameters plus gating of red blood cell and reticulocyte signals based on absorption parameters.

93. The apparatus according to claim 89, wherein the buffer or buffer solution of (b) maintains a reagent composition pH of about 6 to about 9.

94. The apparatus according to claim 89, wherein the buffer or buffer solution of (b) maintains a reagent composition pH of about 7.2 to about 7.5.

95. The apparatus according to claim 89, wherein the dye compound in the reagent composition of (b) is a cationic dye compound.

96. The apparatus according to claim 95, wherein the cationic dye compound is Oxazine 750.

97. The apparatus according to claim 96, wherein Oxazine 750 is present in the reagent composition in an amount of about 2 $\mu$g/ml to about 15 $\mu$g/ml.

98. The apparatus according to claim 95 wherein the cationic dye compound in the reagent composition of (b) is New Methylene Blue.

99. The apparatus according to claim 98, wherein New Methylene Blue is present in the reagent composition in an amount of from about 10 $\mu$g/ml to about 100 $\mu$g/ml.

100. The apparatus according to claim 89, wherein the surfactant in the reagent composition of (b) is selected from the group consisting of nonionic surfactants and zwitterionic surfactants.

101. The apparatus according to claim 100, wherein the surfactant is an alkylglycoside nonionic surfactant.

102. The apparatus according to claim 101, wherein the alkylglycoside nonionic surfactant is selected from the group consisting of n-dodecyl-$\beta$-D-maltoside, n-tetradecyl-$\beta$-D-maltoside and n-tetradecyl-$\beta$-D-glucoside.

103. The apparatus according to claim 100, wherein the surfactant in the reagent composition of (b) is a zwitterionic surfactant.

104. The apparatus according to claim 103, wherein the zwitterionic surfactant in the reagent composition of (b) is an alkyl amido betaine or an alkyl betaine.

105. The apparatus according to claim 104, wherein the zwitterionic surfactant is selected from the group consisting of lauramidopropyl betaine (LAB), cocoamidopropylbetaine (CAPB) and cocoamidosulfobetaine (CASB).

106. The apparatus according to claim 105, wherein lauramidopropyl betaine (LAB) is present in the reagent composition in an amount of from about 12 $\mu$g/ml to about 87.5 $\mu$g/ml; cocoamidopropylbetaine (CAPB) is present in the reagent composition in an amount of from about 8.8 $\mu$g/ml to about 17.5 $\mu$g/ml; and cocoamidosulfobetaine (CASB) is present in the reagent composition in an amount of from about 12.5 $\mu$g/ml to about 15 $\mu$g/ml.

107. The apparatus according to claim 89, wherein the surfactant in the reagent composition of (b) is N-tetradecyl-N,N-dimethyl-3-ammonio-1-propanesulfonate (TDAPS) or N-dodecyl-N,N-dimethyl-3-ammonio-1-propanesulfonate (DDAPS).

108. The apparatus according to claim 107, wherein N-tetradecyl-N,N-dimethyl-3-ammonio-1-propanesulfonate (TDAPS) is present in the reagent composition in an amount of from about 3.9 µg/ml to about 11.8 µg/ml and N-dodecyl-N,N-dimethyl-3-ammonio-1-propanesulfonate (DDAPS) is present in the reagent composition in an amount of from about 49.3 µg/ml to about 148 µg/ml.

109. The apparatus according to claim 89, wherein the reagent composition of (b) further comprises an alkali metal salt.

110. The apparatus according to claim 109, wherein said alkali metal salt in the reagent composition of (b) is sodium chloride or potassium-chloride.

111. The apparatus according to claim 89, wherein the reagent composition of (b) further comprises an antimicrobial compound selected from the group consisting of one or more of 2-methyl-4-isothiazolin-3-one; 5-chloro-2-methyl-4-isothiazolin-3-one; N,N'-methylenebis[N'-(1-(hydroxymethyl)-2,5-dioxo-4-imidazolidinyl]urea); (1-(3-chloroallyl)-3,5,7-triaza-1-azoniaadamantane chloride); and Bronopol 2-bromo-2-nitropropane-1,3-diol ($C_3H_6BrNO_4$).

112. The apparatus according to claim 89, wherein the reagent composition of (b) further comprises at least one nucleophile.

113. The apparatus according to claim 112, wherein said nucleophile is an azide ($N_3^-$) or cyanate ($OCN^-$) ion.

114. The apparatus according to claim 89, wherein the osmolarity of the reagent composition of (b) is about 250 to 300 milliosmoles.

115. The apparatus according to claim 89, wherein the blood sample being analyzed is a normal mammalian blood sample.

116. The apparatus according to claim 89, wherein the qualitative and quantitative parameters determined are selected from the group consisting of red blood cell count, white blood cell count, platelet count, hemoglobin concentration, hematocrit, mean cell volume, mean cell hemoglobin, mean cell hemoglobin concentration, red blood cell volume distribution width, cellular hemoglobin concentration distribution width, mean platelet volume, mean platelet component concentration, mean platelet dry mass, percent and absolute count of neutrophils, percent and absolute counts of lymphocytes plus basophils, percent and absolute count of monocytes, percent and absolute count of eosinophils, percent and absolute count of reticulocytes, reticulocyte mean cell volume, reticulocyte mean cell hemoglobin, reticulocyte mean cell hemoglobin concentration, percent and absolute count of reticulated platelets, mean neutrophil volume, mean neutrophil component concentration, mean neutrophil dry mass, mean lymphocyte+basophil volume, mean lymphocyte+basophil component concentration, mean lymphocyte+basophil dry mass, mean monocyte volume, mean monocyte component concentration, mean monocyte dry mass, mean eosinophil volume, mean eosinophil component concentration and mean eosinophil dry mass.

117. The apparatus according to claim 89, wherein the blood sample of (b) is anticoagulated.

118. The apparatus according to claim 117, wherein the blood sample of (b) is anticoagulated with $K_3$ EDTA.

119. The apparatus according to claim 89, wherein the computer provides cytograms displaying regions occupied by the mature red blood cells; reticulocytes; white blood cells, including lymphocytes, basophils, eosinophils, monocytes and neutrophils; platelets and reticulated platelets discriminated from each other.

120. The apparatus according to claim 119, wherein (i) red blood cells are distinguished from other blood cells in the sample based on regions occupied by the red blood cells in a low-gain, scatter-scatter space on the cytogram; (ii) lymphocytes plus basophils and monocytes are distinguished from other blood cells in the sample based on the regions occupied by the lymphocytes plus basophils and monocytes in a low-gain, scatter-scatter space on the cytogram; (iii) platelets and reticulated platelets are distinguished from other blood cells in the sample based on regions occupied by the platelets in a high-gain, scatter-scatter cytogram; (iv) reticulocytes are distinguished from other blood cells in the sample based on a statistical analysis of an absorption frequency histogram derived from positions occupied by mature red blood cells and reticulocytes in low-gain, high angle absorption space; and (v) neutrophils and eosinophils are distinguished from other blood cells in the sample based on regions occupied by the neutrophils and the eosinophils within scatter-scatter-absorption space.

121. The apparatus according to claim 120, wherein neutrophils are further distinguished from eosinophils based on the regions that neutrophils and eosinophils occupy on a gated low-gain, scatter-scatter cytogram.

122. The apparatus according to claim 89, wherein the blood sample being analyzed is an abnormal mammalian blood sample.

123. A single channel, single dilution method for identifying and measuring cell components in a normal or abnormal mammalian blood sample, comprising mature red blood cells; reticulocytes; white blood cells, including lymphocytes, basophils, eosinophils, monocytes, and neutrophils; platelets and reticulated platelets, and for determining qualitative and quantitative parameters of said blood sample components, comprising:

(a) mixing in a single dilution step an aliquot of the blood sample with an aqueous reagent composition to form a reaction mixture, said reagent composition comprising a surfactant as sphering agent in an amount effective to sphere blood cells in the sample; a dye compound in an amount effective to stain reticulocyte RNA and white blood cell nucleic acid; and a buffer or buffer solution; wherein the red blood cells remain substantially unlysed in the reaction mixture;

(b) passing the reaction mixture of step (a) substantially one cell at a time through a flow cell in a single channel, wherein light is scattered and fluoresced by each cell component; said scattered light being optically detected at a low angle interval of about 1 to 10 degrees to produce a low light scatter intensity measurement and at a high angle interval of about 4 to 30 degrees to produce a high light scatter intensity measurement;

(c) detecting fluorescence signals produced by incident radiation resulting from binding of the dye compound to reticulocyte and white blood cell nucleic acid, or components thereof, in the single channel; and (d) discriminating among and measuring each of the different blood cell components comprising mature red blood cells; reticulocytes; white blood cells, including lymphocytes, basophils, eosinophils, monocytes, and neutrophils; platelets and reticulated platelets of the sample by detecting scatter-scatter optical signals, scatter-fluorescence optical signals, or scatter-scatter-fluorescence optical signals by means of the scattering measurements and fluorescence signals of steps (b) and (c); wherein detection and measurement are performed on each of the cell components flowing through the flow cell in the single channel.

124. The method according to claim 123, wherein, in (b), said low and high scatter intensity measurements undergo a first and second amplification; wherein said first amplification renders signals of the mature red blood cells; reticulocytes; and the white blood cells, including lymphocytes, basophils, eosinophils, monocytes, and neutrophils suitable for analysis, and said second amplification renders signals of the platelets and reticulated platelets suitable for analysis.

125. The method according to claim 123, wherein the low angle interval of (b) is about 1–7 degrees and the high angle interval is about 5–25 degrees.

126. The method according to claim 123, wherein in said discriminating step (d), (i) platelets and reticulated platelets are resolved from other blood cells based on scatter-scatter parameters; (ii) red blood cells are resolved from platelets based on scatter-scatter parameters; (iii) red blood cells are resolved from reticulocytes based on scatter-fluorescence parameters; (iv) red blood cells are resolved from lymphocytes, basophils and monocytes based on scatter-scatter parameters; (v) red blood cells are resolved from neutrophils and eosinophils based on scatter-scatter-fluorescence parameters; (vi) lymphocytes and basophils are resolved from monocytes based on scatter-scatter parameters; and (vii) neutrophils are resolved from eosinophils based on scatter-scatter parameters plus gating of red blood cell and reticulocyte signals based on fluorescence parameters.

127. The method according to claim 123, wherein the buffer or buffer solution of step (a) maintains a reagent composition pH of about 6 to about 9.

128. The method according to claim 123, wherein the buffer or buffer solution of step (a) maintains a reagent composition pH of about 7.2 to about 7.5.

129. The method according to claim 123, wherein the buffer or buffer solution is isotonic, thereby providing substantially isovolumetric sphering of the blood cells.

130. The method according to claim 123, wherein the dye compound in the reagent composition of step (a) is a cationic dye compound.

131. The method according to claim 130, wherein the cationic dye compound is Oxazine 750.

132. The method according to claim 131, wherein Oxazine 750 is present in the reagent composition in an amount of about 2 µg/ml to about 15 µg/ml.

133. The method according to claim 130, wherein the cationic dye compound in the reagent composition of step (a) is New Methylene Blue.

134. The method according to claim 133, wherein New Methylene Blue is present in the reagent composition in an amount of from about 10 µg/ml to about 100 µg/ml.

135. The method according to claim 123, wherein the surfactant in the reagent composition of (a) is selected from the group consisting of nonionic surfactants and zwitterionic surfactants.

136. The method according to claim 135, wherein the surfactant is an alkylglycoside nonionic surfactant.

137. The method according to claim 136, wherein the nonionic surfactant is selected from the group consisting of n-dodecyl-β-D-maltoside, n-tetradecyl-β-D-maltoside and n-tetradecyl-β-D-glucoside.

138. The method according to claim 135, wherein the surfactant in the reagent composition of (a) is a zwitterionic surfactant.

139. The method according to claim 138, wherein the zwitterionic surfactant in the reagent composition of step (a) is an alkyl amido betaine or an alkyl betaine.

140. The method according to claim 139, wherein the zwitterionic surfactant is selected from the group consisting of lauramidopropyl betaine (LAB), cocoamidopropylbetaine (CAPB) and cocoamidosulfobetaine (CASB).

141. The method according to claim 140, wherein lauramidopropyl betaine (LAB) is present in the reagent composition in an amount of from about 12 µg/ml to about 87.5 µg/ml; cocoamidopropylbetaine (CAPB) is present in the reagent composition in an amount of from about 8.8 µg/ml to about 17.5 µg/ml; and cocoamidosulfobetaine (CASB) is present in the reagent composition in an amount of from about 12.5 µg/ml to about 15 µg/ml.

142. The method according to claim 123, wherein the surfactant in the reagent composition of (a) is N-tetradecyl-N,N-dimethyl-3-ammonio-1-propanesulfonate (TDAPS) or N-dodecyl-N,N-dimethyl-3-ammonio-1-propanesulfonate (DDAPS).

143. The method according to claim 142, wherein N-tetradecyl-N,N-dimethyl-3-ammonio-1-propanesulfonate (TDAPS) is present in the reagent composition in an amount of from about 3.9 µg/ml to about 11.8 µg/ml and N-dodecyl-N,N-dimethyl-3-ammonio-1-propanesulfonate (DDAPS) is present in the reagent composition in an amount of from about 49.3 µg/ml to about 148 µg/ml.

144. The method according to claim 123, wherein the reagent composition of step (a) further comprises an alkali metal salt.

145. The method according to claim 123, wherein the reagent composition of step (a) further comprises an antimicrobial compound.

146. The method according to claim 123, wherein said reagent composition of step (a) further comprises at least one nucleophile.

147. The method according to claim 146, wherein said nucleophile is an azide ($N_3^-$) or cyanate ($OCN^-$) ion and is present in said reagent composition at a concentration of about 20 mM.

148. The method according to claim 123, wherein the osmolarity of the reagent composition of (a) is about 250 to 300 milliosmoles.

149. The method according to claim 123, wherein the osmolarity of the reagent composition of step (a) is about 287 to 297 milliosmoles.

150. The method according to claim 123, wherein the blood sample being analyzed is a normal mammalian blood sample.

151. The method according to claim 123, wherein the qualitative and quantitative parameters are selected from the group consisting of red blood cell count, white blood cell count, platelet count, hemoglobin concentration, hematocrit, mean cell volume, mean cell hemoglobin, mean cell hemoglobin concentration, red blood cell volume distribution width, cellular hemoglobin concentration distribution width, mean platelet volume, mean platelet component concentration, mean platelet dry mass, percent and absolute count of neutrophils, percent and absolute counts of lymphocytes plus basophils, percent and absolute count of monocytes, percent and absolute count of eosinophils, percent and absolute count of reticulocytes, reticulocyte mean cell volume, reticulocyte mean cell hemoglobin, reticulocyte mean cell hemoglobin concentration, percent and absolute count of reticulated platelets, mean neutrophil volume, mean neutrophil component concentration, mean neutrophil dry mass, mean lymphocyte+basophil volume, mean lymphocyte+basophil component concentration, mean lymphocyte+basophil dry mass, mean monocyte volume, mean monocyte component concentration, mean monocyte dry mass, mean eosinophil volume, mean eosinophil component concentration and mean eosinophil dry mass.

152. The method according to claim 123, further comprising, following step (d), the step of rinsing the single channel to remove residual cell and reaction mixture accumulation, thereby preventing reagent buildup.

153. The method according to claim 123, wherein the blood sample is anticoagulated.

154. The method according to claim 123, wherein cytograms display the regions occupied by the blood cells and platelets discriminated from each other in the method.

155. The method according to claim 154, wherein (i) red blood cells are distinguished from other blood cells in the sample based on regions occupied by the red blood cells in a low-gain, scatter-scatter space on the cytogram; (ii) lymphocytes+basophils and monocytes are distinguished from other blood cells in the sample based on the regions occupied by the lymphocytes+basophils and monocytes in a low-gain, scatter-scatter space on the cytogram; (iii) platelets and reticulated platelets are distinguished from other blood cells in the sample based on regions occupied by the platelets in a high-gain, scatter-scatter cytogram; (iv) reticulocytes are distinguished from other blood cells in the sample based on a statistical analysis of a fluorescence frequency histogram derived from positions occupied by mature red blood cells and reticulocytes in low-gain, high angle fluorescence space; and (v) neutrophils and eosinophils are distinguished from other blood cells in the sample based on regions occupied by the neutrophils and the eosinophils within scatter-scatter-fluorescence space.

156. The method according to claim 155, wherein neutrophils are further distinguished from eosinophils based on the regions that neutrophils and eosinophils occupy on a gated low-gain, scatter-scatter cytogram.

157. The method according to claim 123, wherein white blood cells are separated from red blood cells in step (d) on the basis of a ratio between wavelength of incident light and refractive index values of the blood cells.

158. The method according to claim 157, wherein the wavelength of incident light at which absorption occurs is narrow banded between 625 to 690 nanometers.

159. The method according to claim 123, wherein the blood sample being analyzed is an abnormal mammalian blood sample.

160. An apparatus for performing a single channel, single dilution method for identifying and measuring cell components comprising mature red blood cells; reticulocytes; white blood cells, including lymphocytes, basophils, eosinophils, monocytes, and neutrophils; platelets and reticulated platelets in a normal or abnormal mammalian blood sample, and for determining qualitative and quantitative parameters of said blood sample components, said apparatus comprising:
  (a) an aspirator mechanism for providing an aliquot of the blood sample;
  (b) a reaction chamber wherein (i) the aliquot of the blood sample is mixed in a single dilution step with an aqueous reagent composition to form a reaction mixture, said reagent composition comprising a dye compound in an amount effective to stain reticulocyte RNA and white blood cell nucleic acid, a surfactant as sphering agent in an amount effective to sphere blood cells and reticulocytes, and a buffer or buffer solution; wherein the red blood cells remain substantially unlysed in the reaction mixture; and (ii) the reaction mixture of (i) comprising the blood cells and platelets is passed substantially one cell at a time through a flow cell in a single optical channel by means of a suitable pump and within a suitable sheathing provided by the pump, wherein light is scattered and fluoresced by each cell component; said scattered light being detected at a low angle interval of about 1 to 10 degrees to produce a low light scatter intensity measurement and at a high angle interval of about 4 to 30 degrees to produce a high light scatter intensity measurement;
  (c) an optical detector for detecting fluorescence signals produced by incident radiation resulting from binding of the dye compound to reticulocyte and white blood cell nucleic acid or components thereof in the single channel; and
  (d) a computer for discriminating among and measuring each of the different blood cell components, comprising mature red blood cells; reticulocytes; white blood cells, including lymphocytes, basophils, eosinophils, monocytes, and neutrophils; platelets and reticulated platelets of the sample by determining scatter-scatter spatial parameters, scatter-fluorescence spatial parameters, or scatter-scatter-fluorescence spatial parameters by using, computing and displaying said scattering measurements and fluorescence signals of (b) and (c); wherein detection and measurement are performed on each of the cell components flowing through the flow cell in the single channel.

161. The apparatus according to claim 160, wherein, in (b)(ii), said low and high scatter intensity measurements undergo a first and second amplification; wherein said first amplification renders signals of the mature red blood cells; reticulocytes; and the white blood cells, including lymphocytes, basophils, eosinophils, monocytes, and neutrophils suitable for analysis, and said second amplification renders signals of the platelets and reticulated platelets suitable for analysis.

162. The apparatus according to claim 160, wherein the low angle interval of (b) is about 1–7 degrees and the high angle interval is about 5–25 degrees.

163. The apparatus according to claim 160, wherein in (d),(i) platelets and reticulated platelets are resolved from other blood cells based on scatter-scatter parameters; (ii) red blood cells are resolved from platelets based on scatter-scatter parameters; (iii) red blood cells are resolved from reticulocytes based on scatter-fluorescence parameters; (iv) red blood cells are resolved from lymphocytes, basophils and monocytes based on scatter-scatter parameters; (v) red blood cells are resolved from neutrophils and eosinophils based on scatter-scatter-fluorescence parameters; (vi) lymphocytes and basophils are resolved from monocytes based on scatter-scatter parameters; and (vii) neutrophils are resolved from eosinophils based on scatter-scatter parameters plus gating of red blood cell and reticulocyte signals based on fluorescence parameters.

164. The apparatus according to claim 160, wherein the buffer or buffer solution of (b) maintains a reagent composition pH of about 6 to about 9.

165. The apparatus according to claim 160, wherein the buffer or buffer solution of (b) maintains a reagent composition pH of about 7.2 to about 7.5.

166. The apparatus according to claim 89 or claim 160, wherein the buffer or buffer solution is isotonic, thereby providing substantially isovolumetric sphering of the blood cells.

167. The apparatus according to claim 160, wherein the dye compound in the reagent composition of (b) is a cationic dye compound.

168. The apparatus according to claim 167, wherein the cationic dye compound is Oxazine 750 or New Methylene Blue.

169. The apparatus according to claim 160, wherein the surfactant in the reagent composition of (b) is selected from the group consisting of nonionic surfactants and zwitterionic surfactants.

170. The apparatus according to claim 169, wherein the nonionic surfactant is an alkylglycoside.

171. The apparatus according to claim 169, wherein the zwitterionic surfactant in the reagent composition of (b) is an alkyl amido betaine or an alkyl betaine.

172. The apparatus according to claim 171, wherein the zwitterionic surfactant is selected from the group consisting of lauramidopropyl betaine (LAB), cocoamidopropylbetaine (CAPB) and cocoamidosulfobetaine (CASB).

173. The apparatus according to claim 160, wherein the surfactant in the reagent composition of (b) is N-tetradecyl-N,N-dimethyl-3-ammonio-1-propanesulfonate (TDAPS) or N-dodecyl-N,N-dimethyl-3-ammonio-1-propanesulfonate (DDAPS).

174. The apparatus according to claim 160, wherein the reagent composition of (b) further comprises an alkali metal salt selected from the group consisting of sodium chloride and potassium chloride.

175. The apparatus according to claim 160, wherein the reagent composition of (b) further comprises an antimicrobial compound selected from the group consisting of one or more of 2-methyl-4-isothiazolin-3-one; 5-chloro-2-methyl-4-isothiazolin-3-one; N,N'-methylenebis[N'-(1-(hydroxymethyl)-2,5-dioxo-4-imidazolidinyl]urea); (1-(3-chloroallyl)-3,5,7-triaza-1-azoniaadamantane chloride); and Bronopol 2-bromo-2-nitropropane-1,3-diol ($C_3H_6BrNO_4$).

176. The apparatus according to claim 160, wherein the reagent composition of (b) further comprises at least one nucleophile.

177. The apparatus according to claim 160, wherein the osmolarity of the reagent composition of (b) is about 250 to 300 milliosmoles.

178. The apparatus according to claim 160, wherein the blood sample being analyzed is a normal mammalian blood sample.

179. The apparatus according to claim 160, wherein the qualitative and quantitative parameters determined are selected from the group consisting of red blood cell count, white blood cell count, platelet count, hemoglobin concentration, hematocrit, mean cell volume, mean cell hemoglobin, mean cell hemoglobin concentration, red blood cell volume distribution width, cellular hemoglobin concentration distribution width, mean platelet volume, mean platelet component concentration, mean platelet dry mass, percent and absolute count of neutrophils, percent and absolute counts of lymphocytes plus basophils, percent and absolute count of monocytes, percent and absolute count of eosinophils, percent and absolute count of reticulocytes, reticulocyte mean cell volume, reticulocyte mean cell hemoglobin, reticulocyte mean cell hemoglobin concentration, percent and absolute count of reticulated platelets, mean neutrophil volume, mean neutrophil component concentration, mean neutrophil dry mass, mean lymphocyte+basophil volume, mean lymphocyte+basophil component concentration, mean lymphocyte+basophil dry mass, mean monocyte volume, mean monocyte component concentration, mean monocyte dry mass, mean eosinophil volume, mean eosinophil component concentration and mean eosinophil dry mass.

180. The apparatus according to claim 160, wherein the computer provides cytograms displaying regions occupied by the mature red blood cells; reticulocytes; white blood cells, including lymphocytes, basophils, eosinophils, monocytes, and neutrophils; platelets and reticulated platelets discriminated from each other.

181. The apparatus according to claim 180, wherein (i) red blood cells are distinguished from other blood cells in the sample based on regions occupied by the red blood cells in a low-gain, scatter-scatter space on the cytogram; (ii) lymphocytes plus basophils and monocytes are distinguished from other blood cells in the sample based on the regions occupied by the lymphocytes plus basophils and monocytes in a low-gain, scatter-scatter space on the cytogram; (iii) platelets and reticulated platelets are distinguished from other blood cells in the sample based on regions occupied by the platelets in a high-gain, scatter-scatter cytogram; (iv) reticulocytes are distinguished from other blood cells in the sample based on a statistical analysis of a fluorescence frequency histogram derived from positions occupied by mature red blood cells and reticulocytes in low-gain, high angle fluorescence space; and (v) neutrophils and eosinophils are distinguished from other blood cells in the sample based on regions occupied by the neutrophils and the eosinophils within scatter-scatter-fluorescence space.

182. The apparatus according to claim 181, wherein the neutrophils are further distinguished from the eosinophils based on the regions that neutrophils and eosinophils occupy on a gated low-gain, scatter-scatter cytogram.

183. The apparatus according to claim 160, wherein the blood sample being analyzed is an abnormal mammalian blood sample.

184. A single channel, single dilution method for identifying and measuring cell components in a normal or abnormal mammalian blood sample, comprising mature red blood cells; reticulocytes; white blood cells, including lymphocytes, basophils, eosinophils, monocytes, and neutrophils; platelets and reticulated platelets, and for determining qualitative and quantitative parameters of said blood sample components, comprising:

(a) mixing in a single dilution an aliquot of the blood sample with an aqueous reagent composition to form a reaction mixture, said reagent composition comprising a surfactant as sphering agent in an amount effective to sphere blood cells in the sample; a dye compound in an amount effective to stain reticulocyte RNA and white blood cell nucleic acid; and a buffer or buffer solution; wherein the red blood cells remain substantially unlysed in the reaction mixture;

(b) passing the reaction mixture of (a) substantially one cell at a time through a flow cell in a single channel, wherein light is scattered and either (i) absorbed or (ii) fluoresced by each cell component; said scattered light being optically detected and amplified to render light scattering signals of the mature red blood cells; reticulocytes; white blood cells, including lymphocytes, basophils, eosinophils, monocytes, and neutrophils; platelets; and reticulated platelets suitable for analysis as each cell type passes through the flow cell in the single channel;

(c) detecting either (i) absorption or (ii) fluorescence signals produced by incident radiation resulting from binding of the dye compound to reticulocyte and white blood cell nucleic acid, or components thereof, in the single channel; and (d) discriminating among and measuring each of the different blood cell components, comprising mature red blood cells; reticulocytes; white blood cells, including lymphocytes, basophils, eosinophils, monocytes, and neutrophils; platelets and reticulated platelets of the sample, by detecting optical signals selected from either (i) scatter-scatter optical signals, scatter-absorption optical signals, or scatter-scatter-absorption optical signals by means of the scattering and absorption signals of steps (b) and (c); or (ii) scatter-scatter optical signals, scatter-fluorescence optical signals, or scatter-scatter-fluorescence optical signals by means of the scattering and fluorescence signals of steps (b) and (c); wherein detection and measurement are performed on each of the cell components comprising mature red blood cells; reticulocytes; white blood cells, including lymphocytes, basophils, eosinophils, monocytes, and neutrophils; platelets and reticulated platelets flowing through the flow cell in the single channel of a cytometry analyzer.

185. An apparatus for performing a single channel, single dilution method for identifying and measuring cell components in a normal or abnormal mammalian blood sample, comprising mature red blood cells; reticulocytes; white blood cells, including lymphocytes, basophils, eosinophils, monocytes, and neutrophils; platelets; and reticulated platelets, and for determining qualitative and quantitative parameters of said blood sample components, comprising:

(a) an aspirator mechanism for providing an aliquot of the blood sample;

(b) a reaction chamber wherein (i) the aliquot of the blood sample is mixed in a single dilution step with an aqueous reagent composition to form a reaction mixture, said reagent composition comprising a surfactant as sphering agent in an amount effective to sphere blood cells in the sample; a dye compound in an amount effective to stain reticulocyte RNA and white blood cell nucleic acid; and a buffer or buffer solution; wherein the red blood cells remain substantially unlysed in the reaction mixture; and (ii) the reaction mixture of (i) is passed substantially one cell at a time through a flow cell in a single optical channel of the apparatus by means of a suitable pump and within a suitable sheathing provided by the pump, wherein light is scattered and either (i) absorbed or (ii) fluoresced by each cell component; said scattered light being optically detected and amplified to render light scattering signals of the mature red blood cells; reticulocytes; white blood cells, including lymphocytes, basophils, eosinophils, monocytes, and neutrophils; platelets and reticulated platelets suitable for analysis as each cell type passes through the flow cell in the single channel;

(c) an optical detector for detecting either (i) absorption or (ii) fluorescence signals produced by incident radiation resulting from binding of the dye compound to reticulocyte and white blood cell nucleic acid, or components thereof, in the single channel; and (d) a computer for discriminating among and measuring each of the different blood cell components, comprising mature red blood cells; reticulocytes; white blood cells, including lymphocytes, basophils, eosinophils, monocytes, and neutrophils; platelets and reticulated platelets of the sample, by detecting optical signals selected from either (i) scatter-scatter optical signals, scatter-absorption optical signals, or scatter-scatter-absorption optical signals by means of the scattering and absorption signals of steps (b) and (c); or (ii) scatter-scatter optical signals, scatter-fluorescence optical signals, or scatter-scatter-fluorescence optical signals by means of the scattering and fluorescence signals of steps (b) and (c); wherein detection and measurement are performed on each of the cell components as each cell type flows through the flow cell in the single channel.

* * * * *